United States Patent [19]
Ozaki et al.

[11] Patent Number: 6,010,891
[45] Date of Patent: Jan. 4, 2000

[54] PROCESS FOR PRODUCING CIS-3-HYDROXY-L-PROLINE

[75] Inventors: Akio Ozaki; Hideo Mori; Takeshi Shibasaki; Katsuhiko Ando, all of Machida; Keiko Ochiai, Ebina; Shigeru Chiba, Kawasaki; Yoichi Uosaki, Machida, all of Japan

[73] Assignee: Kyowa Hakko Kogyo, Co, Ltd., Tokyo, Japan

[21] Appl. No.: 09/287,375

[22] Filed: Apr. 7, 1999

Related U.S. Application Data

[60] Division of application No. 08/708,856, Sep. 9, 1996, which is a continuation-in-part of application No. 08/474,135, Jul. 6, 1995, abandoned, which is a continuation-in-part of application No. 08/301,654, Sep. 7, 1994, abandoned.

[30] Foreign Application Priority Data

Sep. 7, 1993 [JP] Japan .................................. 5-221941

[51] Int. Cl.[7] ................................ C12N 9/02; C12N 1/20; C12N 15/00; C07H 21/04; C07K 1/00
[52] U.S. Cl. ................... 435/189; 435/252.3; 435/320.1; 435/107; 536/23.2; 530/350
[58] Field of Search ................................ 435/189, 252.3, 435/320.1, 107; 536/23.2; 530/350

Primary Examiner—Ponnathapu Achutamurthy
Assistant Examiner—Tekchand Saidha
Attorney, Agent, or Firm—Antonelli, Terry, Stout & Kraus, LLP

[57] ABSTRACT

An industrially applicable process for producing cis-3-hydroxy-L-proline, which is useful as a raw material for medicines or as an additive to foods. In the process, L-proline is converted into cis-3-hydroxy-L-proline in the presence of an enzyme source which is derived from a microorganism belonging to the genus Streptomyces or Bacillus and which catalyzes hydroxylation of L-proline into cis-3-hydroxy-L-proline, a divalent iron ion and 2-ketoglutaric acid, in an aqueous medium, and the produced cis-3-hydroxy-L-proline is collected from the aqueous medium. A novel enzyme L-proline-3-hydroxylase, a gene of L-proline-3-hydroxylase which is useful for the process, a transformant containing the gene, and a process for producing L-proline-3-hydroxylase using the transformant, is also provided.

23 Claims, 7 Drawing Sheets

PROCESS FOR PRODUCING CIS-3-HYDROXY-L-PROLINE

This application is a division of Ser. No. 08/708,856, which is a continuation-in-part of Ser. No. 08/474,135, filed Jul. 6, 1995, now abandoned, which is continuation-in-part of Ser. No. 08/301,654 filed Sep. 7, 1994, now abandoned.

FIELD OF THE INVENTION

The present invention relates to a process for producing cis-3-hydroxy-L-proline. Cis-3-hydroxy-L-proline is useful as a starting compound for medicines and an additive to foods. The present invention also relates to a novel enzyme capable of catalyzing the hydroxylation of L-proline at the 3-position of L-proline (hereinafter referred to as "L-proline-3-hydroxylase"). The novel enzyme is used in the above-mentioned process.

The present invention also relates to a gene encoding a protein having an activity of L-proline-3-hydroxylase (hereinafter referred to as "L-proline-3-hydroxylase gene") which is useful for the above-mentioned process, a transformant containing the gene, and a process for producing L-proline-3-hydroxylase using the transformant.

BACKGROUND OF THE INVENTION

Heretofore, chemosynthetic methods of producing cis-3-hydroxy-L-proline are known [J. Amer. Chem. Soc., 84, 3980 (1962); J. Amer. Chem. Soc., 85, 2824 (1963); Nature 289, 310 (1981); J. Org. Chem., 54, 1866 (1989); Acta Chemica Scandinavica, 43, 290 (1989)].

The conventional chemosynthetic methods for producing cis-3-hydroxy-L-proline are not satisfactory for industrial production, because of (1) the expensive raw materials, (2) too many reaction steps, (3) the complicated procedures for isolating and purifying the product and/or (4) the lower productivity of cis-3-hydroxy-L-proline.

No chemosynthetic or biological method of producing cis-3-hydroxy-L-proline by hydroxylating L-proline both regio-selectively and stereo-selectively, has been reported.

The object of the present invention is to provide an advantageous process for the production of cis-3-hydroxy-L-proline which is industrially applicable, and a second object of the present invention is to provide a novel enzyme which catalyzes the hydroxylation of L-proline at the 3-position of L-proline and which is useful in the above process.

SUMMARY OF THE INVENTION

The present invention provides a process for producing cis-3-hydroxy-L-proline, which comprises allowing L-proline to coexist with 2-ketoglutaric acid, a divalent iron ion and an enzyme source which catalyzes the hydroxylation of L-proline at the 3-position of L-proline in an aqueous medium to convert L-proline into cis-3-hydroxy-L-proline, and recovering the cis-3-hydroxy-L-proline from the aqueous medium.

The present invention further provides a novel hydroxylase (L-proline-3-hydroxylase) having the following physicochemical properties:
(1) Action and Substrate Specificity
  The enzyme catalyzes the hydroxylation of L-proline at the 3-position of L-proline in the presence of 2-ketoglutaric acid and a divalent iron ion to produce cis-3-hydroxy-L-proline.
(2) Optimum pH Range
  The enzyme has an optimum pH range of 6.5 to 7.5, for its reaction at 30° C. for 20 minutes.
(3) Stable pH Range
  The enzyme is stable at pH values of 6.5 to 8.0, when it is allowed to stand at 4° C. for 23 hours.
(4) Optimum Temperature Range
  The optimum temperature range is 35 to 40° C. when it is allowed to stand at pH 7.0 for 15 minutes.
(5) Stable Temperature Range
  The enzyme is inactivated, when it is allowed to stand at pH 7.5 and at 50° C. for 30 minutes.
(6) Inhibitors
  The activity of the enzyme is inhibited by metal ions of $Zn^{++}$, $Cu^{++}$, $Co^{++}$ and $Ba^{++}$ and ethylenediaminetetraacetic acid (EDTA).
(7) Activation
  The enzyme does not need any cofactor for its activation. L-Ascorbic acid accelerates the activity of the enzyme.
(8) Km Value
  The Km value is 0.49 mM for L-proline and is 0.11 mM for 2-ketoglutaric acid, when determined in a 100 mM N-tris(hydroxymethyl)methyl-2-aminoethansulfonic acid (TES) buffer (pH 7.0) containing 5 mM L-ascorbic acid, 1 mM ferrous sulfate and a pre-determined amount of this enzyme.
(9) Isoelectric Point
  The enzyme has an isoelectric point of 4.3 as determined by the Phast system.
(10) Molecular Weight
  The enzyme has a molecular weight of 35,000±5,000 daltons as determined by sodium dodecylsulfate-polyacrylamide gel electrophoresis.
(11) N-terminal Amino Acid Sequence
  The enzyme has an N-terminal amino acid sequence illustrated by Sequence No: 5.
Sequence No: 5
(N-terminal)
  1 MetArgSerHisIleLeuGlyArgIleGlu
  11 LeuAspGlnGluArgLeuGlyArgAspLeu
  21 GluTyrLeuAlaThrValProThrVal The present invention provides an L-proline-3-hydroxylase gene and a transformant containing the gene for the purpose of producing cis-3-hydroxy-L-proline efficiently and industrially using L-proline-3-hydroxylase from L-proline that is available at low cost, a process for mass-producing the L-proline-3-hydroxylase using the transformant containing the gene, and a process for producing cis-3-hydroxy-L-proline industrially at low cost using a transformant containing the gene conding for L-proline-3-hydroxylase.

In this, the thick, solid black lines each indicate a cloned Streptomyces sp. TH1 chromosome site. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmids are shown.

Figure 2:
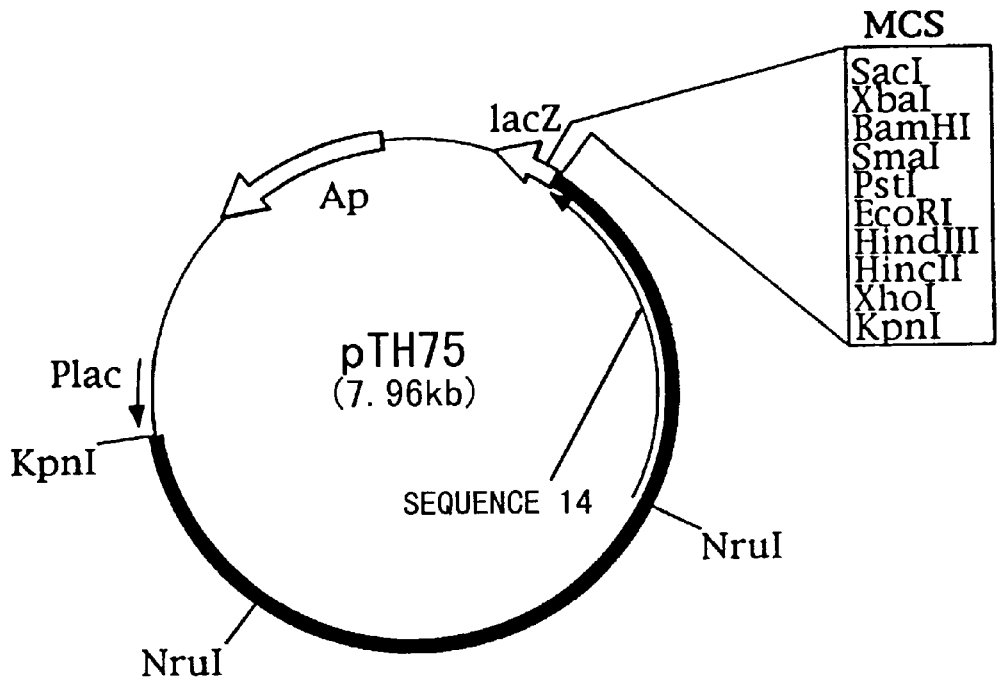
Figure 2:
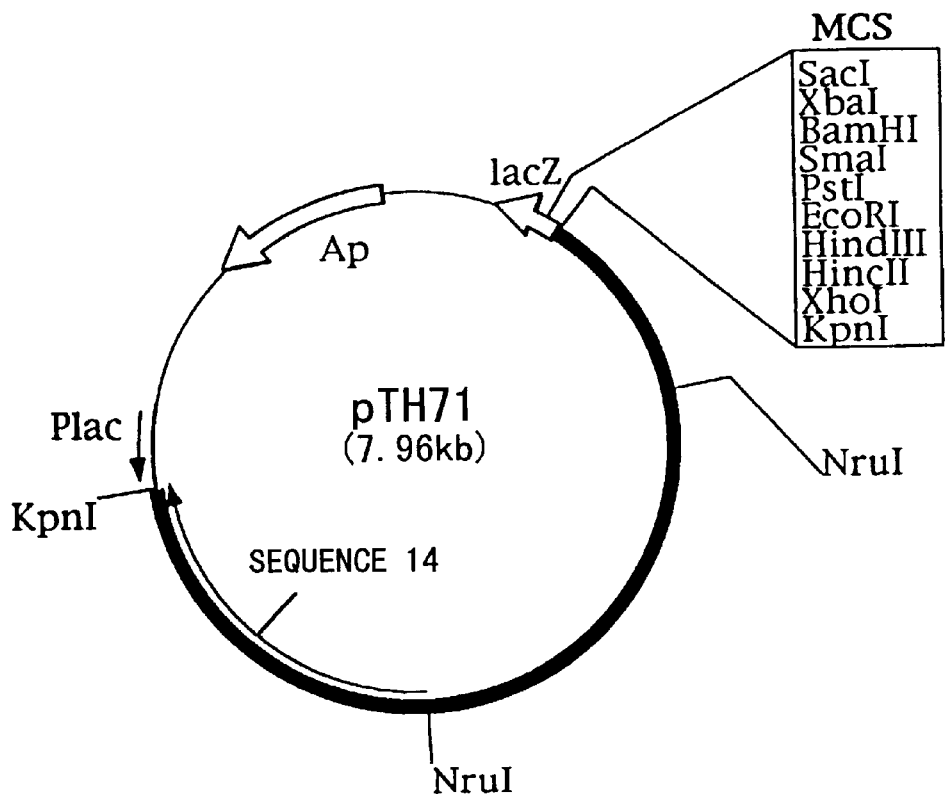

FIG. 2 shows plasmid pTH71 and plasmid pTH75.

In this, the thick, solid black lines each indicate a cloned Streptomyces sp. TH1 chromosome site. At the part of the thick, solid black line as drawn along with an arrow, the site has the base sequence corresponding to SEQ ID No: 14. The direction of each arrow indicates the direction toward the terminal of the sequence of SEQ ID No. 14 from the head thereof. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmids are shown.

Figure 3:
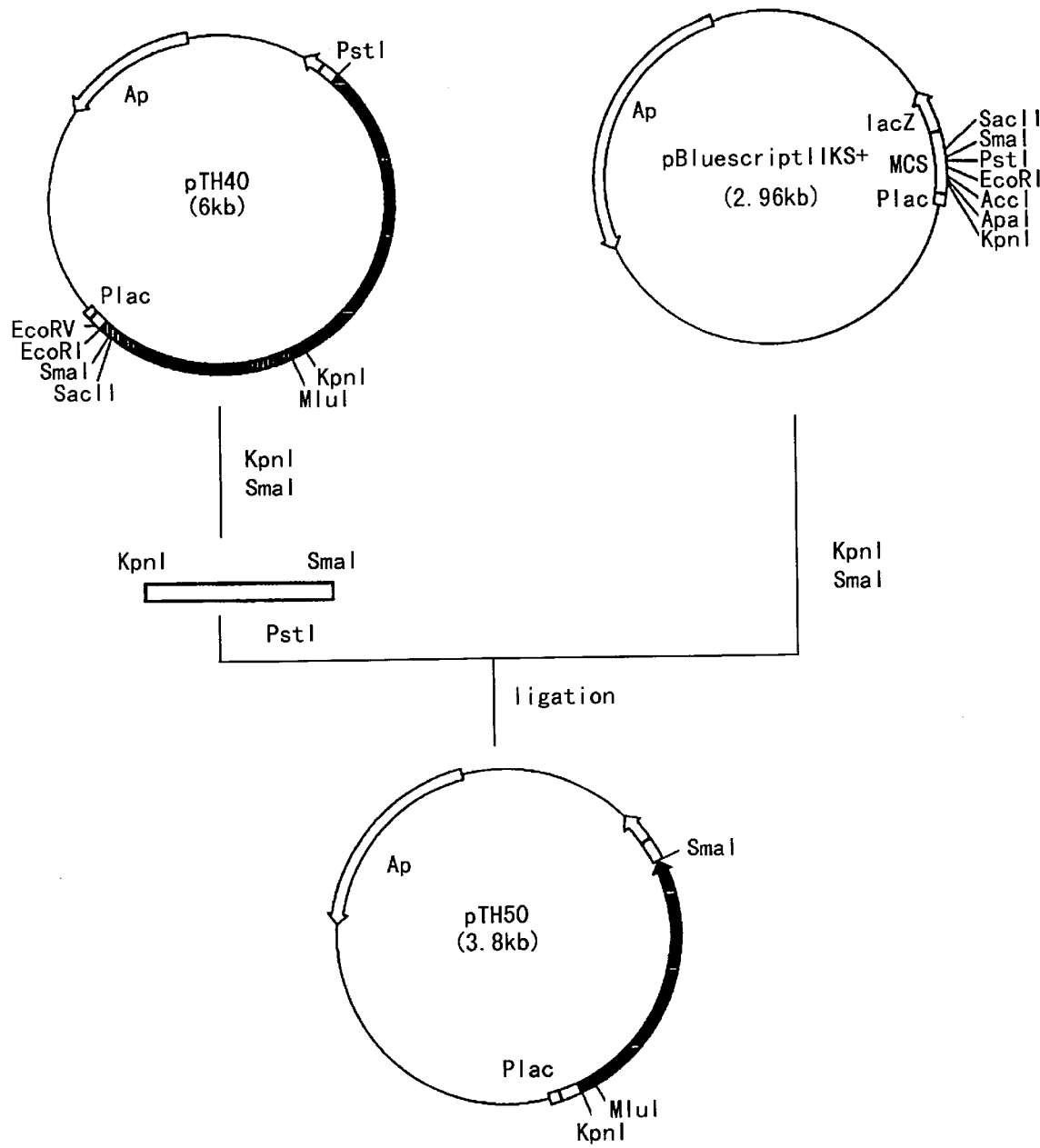

FIG. 3 shows the steps of constructing plasmid pTH50.

In this, the thick, solid black lines each indicate a part containing a Streptomyces sp. TH1 chromosome site-derived L-proline-3-hydroxylase gene. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmid are shown.

Figure 4:
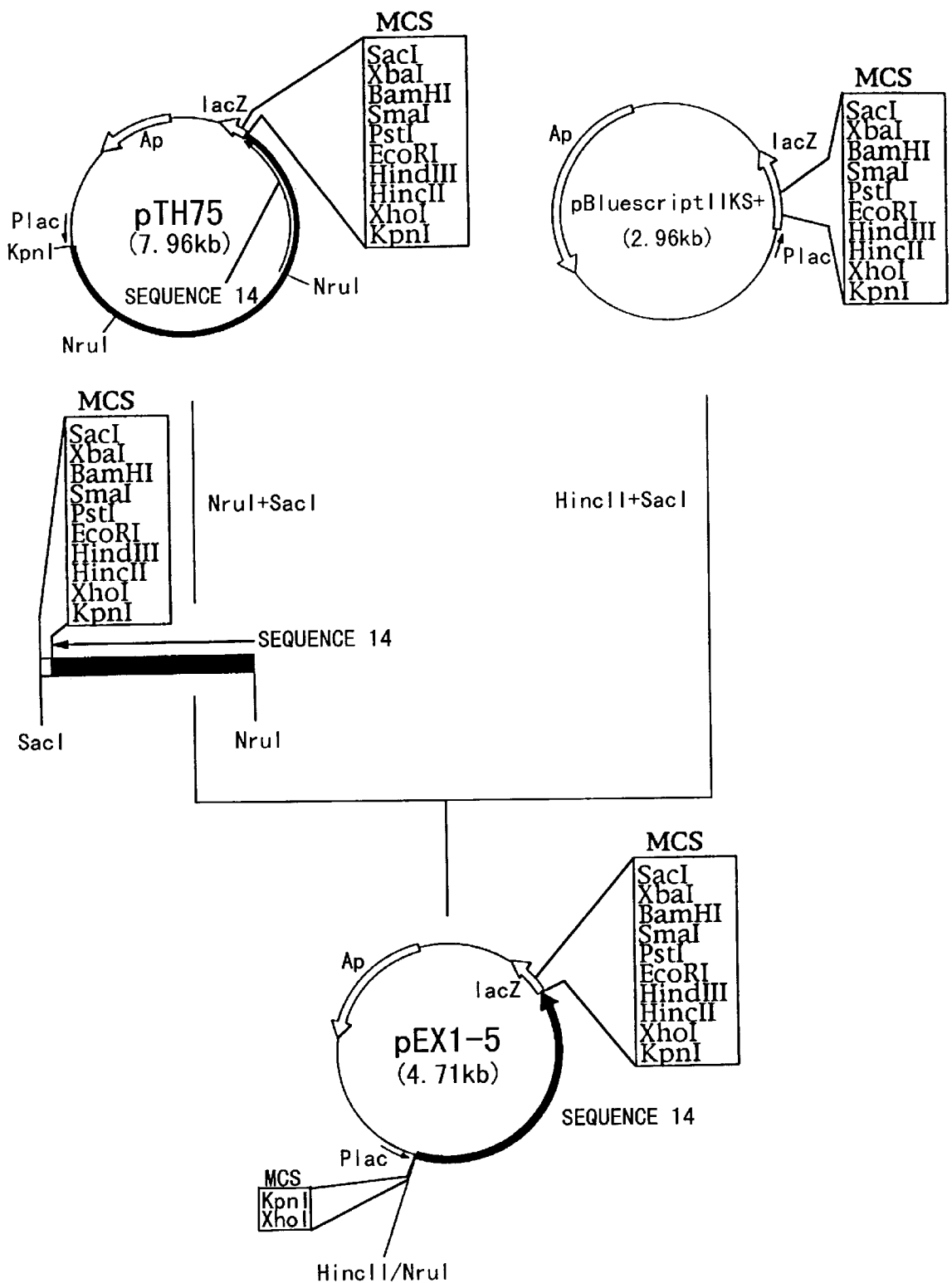

FIG. 4 shows the steps of constructing plasmid pEX1-5.

In this, the thick, solid black lines each indicate a part containing a Streptomyces sp. TH1 chromosome site-derived L-proline-3-hydroxylase gene. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmid are shown.

Figure 5:
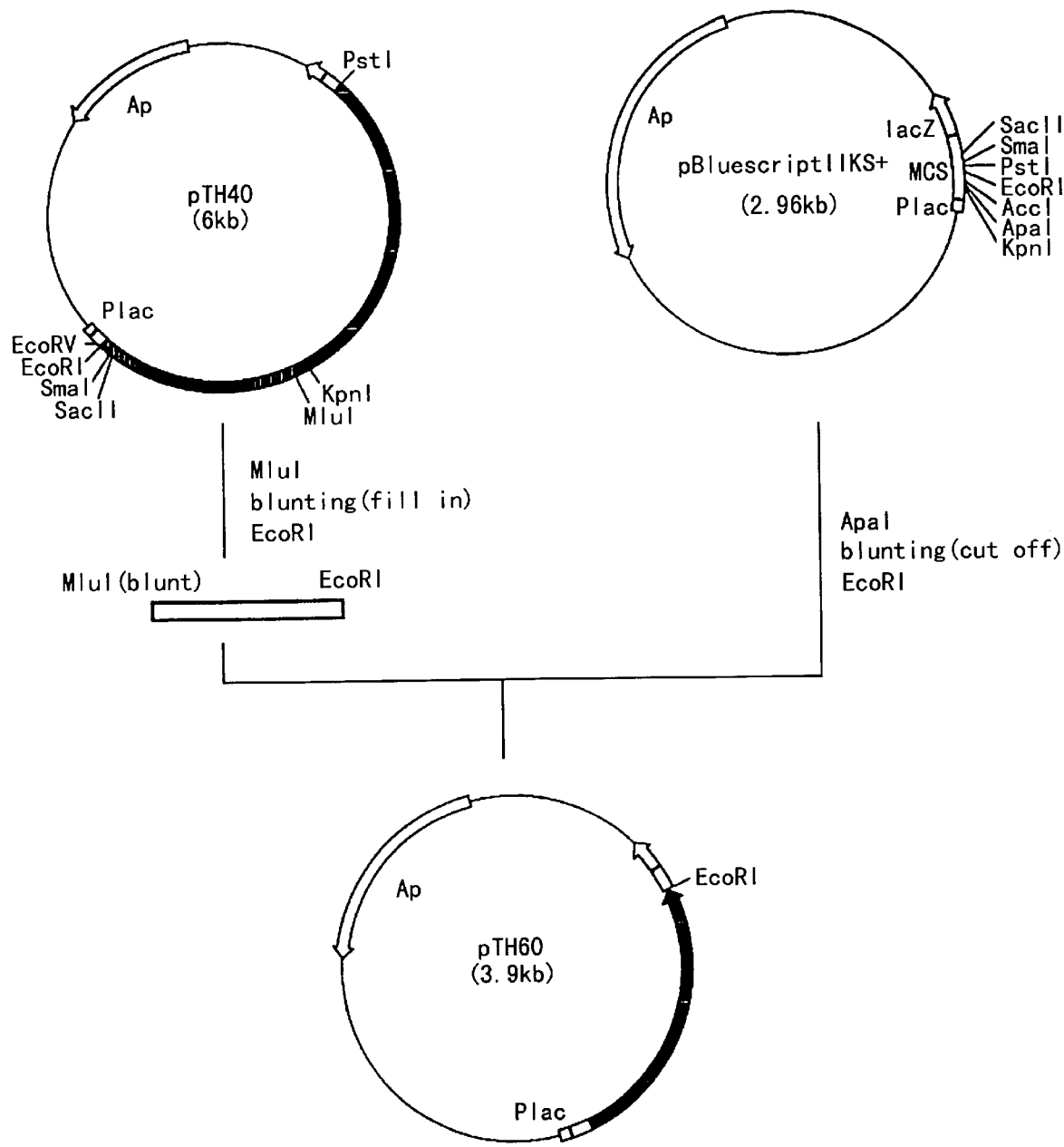

FIG. 5 shows the steps of constructing plasmid pTH60.

In this, the thick, solid black lines each indicate a part containing a Streptomyces sp. TH1 chromosome site-derived L-proline-3-hydroxylase gene. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmid are shown.

Figure 6:
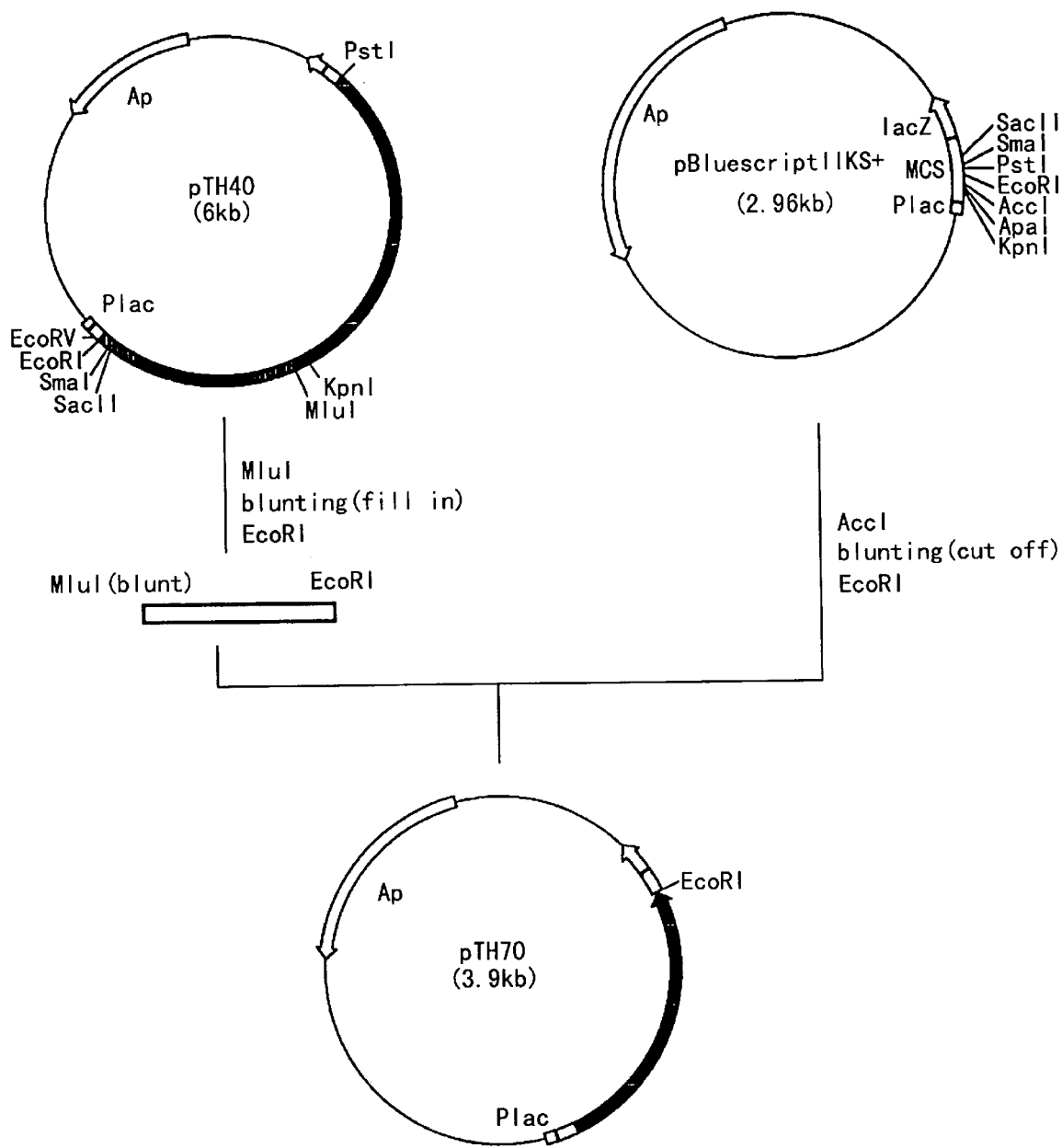

FIG. 6 shows the steps of constructing plasmid pTH70.

In this, the thick, solid black lines each indicate a part containing a Streptomyces sp. TH1 chromosome site-derived L-proline-3-hydroxylase gene. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmid are shown.

Figure 7:
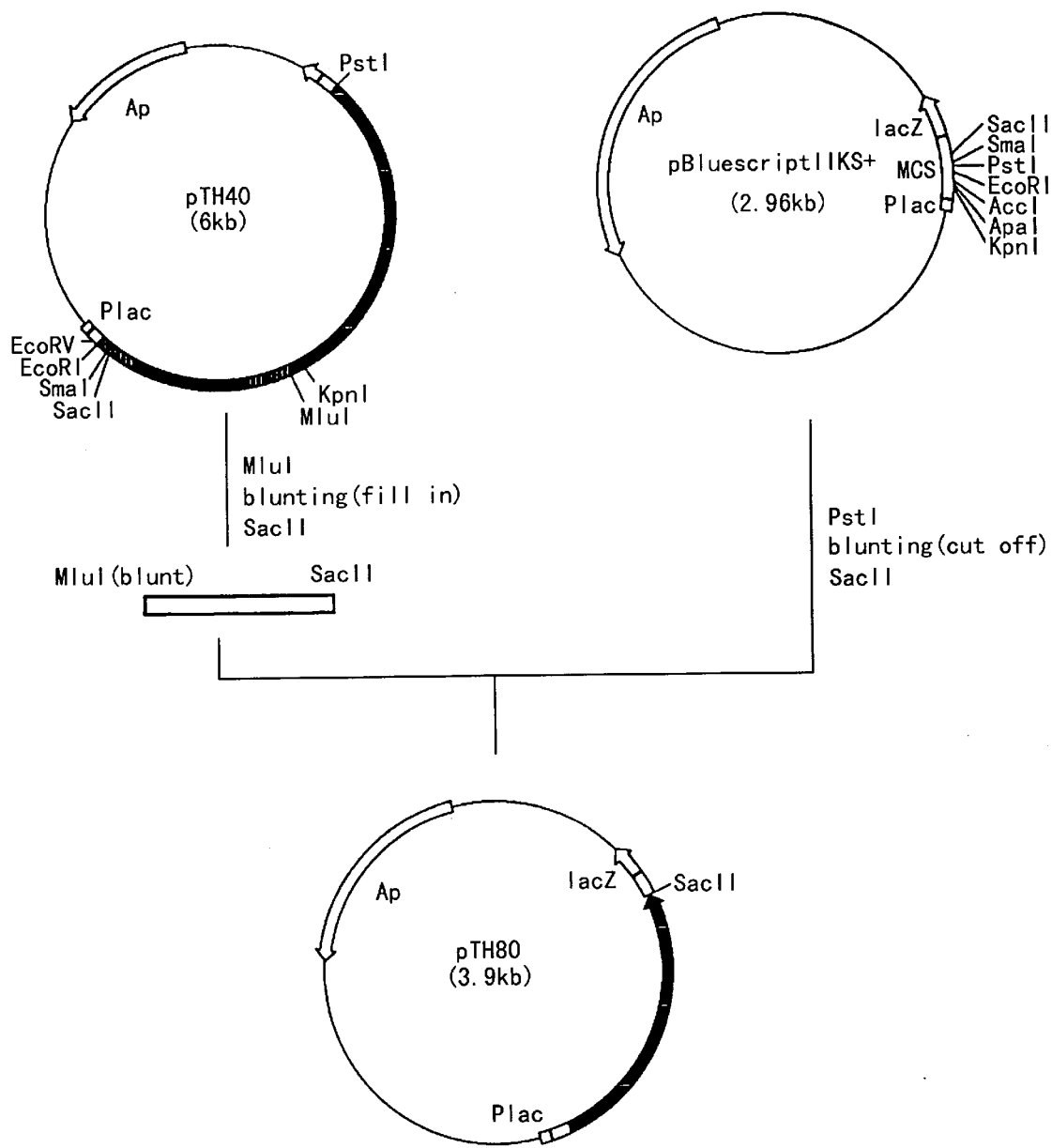

FIG. 7 shows the steps of constructing plasmid pTH80.

In this, the thick, solid black lines each indicate a part containing a Streptomyces sp. TH1 chromosome site-derived L-proline-3-hydroxylase gene. Ap indicates a pBR322-derived ampicillin-resistant gene. Plac indicates an *Escherichia coli* lactose promoter; lacZ indicates a β-galactosidase structural gene; and MCS indicates a multi-cloning site. In this, only the restriction enzyme sites related to the construction of the plasmid are shown.

DETAILED DESCRIPTION OF THE INVENTION

As the enzyme source to be used in the process for producing cis-3-hydorxy-L-proline of the present invention, any microorganism can be used so long as it has an enzymatic activity of catalyzing the hydroxylation of L-proline at the 3-position of L-proline in the presence of 2-ketoglutaric acid and a divalent iron ion. As the microorganism having such activity, mention may be made of microorganisms belonging to the genus Streptomyces or Bacillus. The preferred strain of such microorganism includes *Streptomyces canus* ATCC 12647, *Streptomyces canus* ATCC 12646, Streptomyces sp. TH1, and Bacillus sp. TH2 and TH3. Specifically, a culture, cells or processed cells of these strains can be used. Further, a crude enzyme preparation from cells of the microorganism as mentioned above, a purified product of such enzyme preparation, an immobilized enzyme preparation, etc. can be used.

Streptomyces sp. TH1 was newly isolated by the present inventors from the soil. The bacteriological properties of the strain TH1 is mentioned below.

1. Morphological Properties

The morphological properties of the strain when cultivated on various media at 28° C. for 14 days are shown in Table 1 below.

TABLE 1

| | Morphological Properties | | |
|---|---|---|---|
| 1) Hyphae | Formation of aerial hyphae: | Yes | |
| | Fragmentation and motility of aerial hyphae: | Not observed | |
| | Fragmentation and motility of substrate hyphae: | Not observed | |
| 2) Spores | Sporulation and Positions to which spores adhere: | Adhered to aerial hyphae | |
| | Formation of sparangia: | Not observed | |
| | Number of spores on its aerial mycelium: | More than 10 | |
| | Appearance of spore chain: | Spiral | |
| | Characteristics of spores Surface structure: | Spiny | |
| | Shape and size: | Ellipsoidal, 0.5~0.7 × 1.0~1.2 μm | |
| | Motility and fragella: | Not observed | |
| 3) Others | Chlamydospores: | Not observed | |
| | Synnemata: | Not observed | |
| | Pseudosporangia: | Not observed | |
| | Branching mode of hyphae: | Simple branching | |

2. Cultural Characteristics in Various Media

The strain TH1 grows normally or vigorously on usual synthetic and natural media, while its substrate hyphae are pale pink (rose), orange or greenish brown. On some media, the strain often produces brown or blackish soluble pigments.

The cultural characteristics of the strain TH1, when the strain was cultivated on various media at 28° C. for 14 days, are shown in Table 2. The designation of the colors has been made, according to the classification of colors indicated in Color Harmony Manual published by Container Corporation of America.

TABLE 2

| Cultural Characteristics in Various Media | | |
|---|---|---|
| 1) Sucrose-nitrate agar | Growth: | Moderate |
| | Color of substrate hyphae; | Pearl pink (3 ca) |
| | Adhesion of aerial hyphae: | None |
| | Soluble pigments: | None |
| 2) Glucose-asparagine agar | Growth: | Moderate |
| | Color of substrate hyphae; | Pearl pink (3 ca) |
| | Adhesion of aerial hyphae: | None |
| | Soluble pigments: | None |

TABLE 2-continued

Cultural Characteristics in Various Media

| | | |
|---|---|---|
| 3) Glycerol-asparagine agar | Growth: | Moderate |
| | Color of substrate hyphae; | Pearl pink~bright orange (3ca~4na) |
| | Adhesion and color of aerial hyphae: | Poor, white (a) |
| | Soluble pigments: | Produced only a little (Pale yellow) |
| 4) Inorganic salts-starch agar | Growth: | Moderate |
| | Color of substrate hyphae: | Pearl (2 ba) |
| | Adhesion and color of aerial hyphae: | Moderate, white (a) |
| | Soluble pigments: | Negative |
| 5) Tyrosine agar | Growth: | Moderate |
| | Color of substrate hyphae: | Light olive (1 1/2 ie) |
| | Adhesion and color of aerial hyphae: | Moderate, white~olive gray |
| | Soluble pigments: | Produced (black) |
| 6) Nutrient agar | Growth: | Poor |
| | Color of substrate hyphae: | Light melon yellow (3 ea) |
| | Adhesion of aerial hyphae; | None |
| | Soluble pigments: | None |
| 7) Yeast extract-malt extract agar | Growth: | Abundant |
| | Color of substrate hyphae: | Flesh pink (4 ca) |
| | Adhesion and color of aerial hyphae: | Moderate, white (a) |
| | Soluble pigments: | Produced only a little (ocher) |
| 8) Oatmeal agar | Growth; | Poor |
| | Color of substrate hyphae: | Yellow tint (1 ba) |
| | Adhesion and color of aerial hyphae: | Moderate, white (a) |
| | Soluble pigments: | None |

3. Physiological Properties

The physiological properties of the strain TH1 is shown in Table 3, in which the "temperature range for growth" indicates the results of the strain after 7 day-cultivation by shaking. The remaining items indicate the results after 2 to 3 week-cultivation at 28° C.

TABLE 3

Physiological Properties

| | |
|---|---|
| 1)Temperature Range for Growth | 23 to 37° C. |
| 2)Liquefaction of Gelatin | No |
| 3)Hydrolysis of Starch | Yes |
| 4)Coagulation of Skim Milk Powder | No |
| 5)Peptonization of Skim Milk Powder | No |
| 6)Formation of Melanoid Pigments | |
| (1) Peptone-yeast extract-iron agar | Yes |
| (2) Tyrosine agar | Yes |
| 7)Utilization of Carbon Sources(*) | |
| L-Arabinose | + |
| D-Glucose | + |
| D-Xylose | + |
| Sucrose | + |
| Raffinose | + |
| D-Fructose | + |
| Rhamnose | − |
| Inositol | + |
| D-Mannitol | + |

(*) As the basic medium, used was Pridham Gottlieb-agar medium.
+ indicates that the strain utilized the carbon source;
− indicates that the strain did not utilize the carbon source.

4. Chemotaxonomic Properties

The configuration of diaminopimelic acid in the cells is LL type. Accordingly, the strain TH1 is classified to the genus Streptomyces of actinomycetes in view of its morphological property that it forms spiral spore chain consisting of more than ten spores on its aerial mycelium, and in view of its chemotaxonomic property that the diaminopimelic acid contained in its cell wall is L,L-diaminopimelic acid (type I).

The strain TH1 was identified as Streptomyces sp. TH1, and the strain has been deposited with the National Institute of Bioscience and Human-Technology, Agency of Industrial Science and Technology in Japan as of Sep. 1, 1993 under FERM BP-4399 in terms of the Budapest Treaty.

Bacillus sp. TH2 and TH3 were newly isolated by the present inventors from the soil. The bacteriological properties of strains TH2 and TH3 are mentioned below.

Both strains TH2 and TH3 are the same in the following properties, except that the cell sizes of the strain TH2 and TH3 are 1.5 to 1.8×3 to 4 μm and 1.2 to 1.5×3.5 to 4 μm, respectively, and the base compositions of DNA (G+C mol %) of the strains TH2 and TH3 are 36.46% and 37.74%, respectively.

1. Morphological Properties

The strains had the morphological properties shown in Table 4 below.

TABLE 4

Morphological Properties

| | | |
|---|---|---|
| 1) Cells | Morphology | Rod |
| | Polymorphism | Not observed |
| | Motility (Position of flagella) | Not observed |
| 2) Endo Spores | Sporulation | Observed |
| | Morphology | Ellipse |
| | Positions | The end position |

2. Cultural Characteristics in Various Media

The Cultural characteristics of the strains TH2 and TH3 are shown in Table 5 below.

TABLE 5

Cultural Characteristics in Various Media

| | | |
|---|---|---|
| Bouillon-Agar Medium (Meat extract) | Growth | Abundant |
| | Shape of surface | Smooth |
| | Color | Pale yellow white |
| | Gloss | None |
| | Diffusible pigments | Negative |
| Bouillon-liquid Medium (Meat extract) | Growth appearance | Grown only a little on surface of the medium |
| | Turbidity | Positive |
| Bouillon-Gelatin-medium | Liquefaction of gelatin | Positive |
| Litmus milk | Reaction | Acid |
| | Coagulation | Negative |
| | Liquefaction | Positive |

3. Physiological Properties

The physiological properties of the strains TH2 and TH3 are shown in Table 6.

TABLE 6 (1)

Physiological Properties

| | | | |
|---|---|---|---|
| (1)Gram staining | + | (11)Pigment production | |
| (2)Reduction to nitrite | + | King A medium | − |
| (3)Denitrification | + | King B medium | − |

TABLE 6 (1)-continued

Physiological Properties

| reaction | (12)Urease | − |
|---|---|---|
| (4)Methyl red test | (13)Oxidase | − |
| (5)VP test | (14)Catalase | + |
| (6)Indole production | (15)Growth range | |
| (7)Hydrogen sulfide production | pH; | 5 to 9.7 |
| | Optimum pH; | 7.1 |
| (8)Hydrolysis of starch | Temperature; | 4 to 36° C. |
| (9)Utilization of citric acid Koser's method | Optimum temp; | around 33° C. |
| | (16)Attitude towards oxygen | |
| Christensen's method | Aerobic | W |
| (10)Utilization of inorganic nitrogen | Anaerobic (facultative | + |
| Nitrates | anaerobic) | − |
| Ammonium salts | (17)OF test | + oxidation |

+: Positive, −:Negative, W: Weak

TABLE 6 (2)

Production of Acid and Gas from Carbohydrates

| | Acid production | Gas production |
|---|---|---|
| L-Arabinose | − | − |
| D-Xylose | − | − |
| D-Glucose | + | − |
| D-Mannose | − | − |
| D-Fructose | + | − |
| D-Galactose | − | − |
| Maltose | + | − |
| Sucrose | + | − |
| Lactose | − | − |
| Trehalose | + | − |
| D-Sorbitol | − | − |
| D-Mannitol | − | − |
| Inositol | − | − |
| Glycerol | − | − |
| Starch | + | − |

+: Positive −: Negative

4. The Other Properties and the Chemotaxonomic Properties

The other properties of the strains TH2 and TH3 are shown in Table 7, and the chemotaxonomic properties are shown in Table 8 below.

TABLE 7

Other Properties

| Degradation of Esculin | + |
|---|---|
| Degradation of Malonic acid | − |
| Degradation of Arginine | + |
| Decarboxylation of Lysine | − |
| Decarboxylation of Ornithine | − |
| Deamination of Phenylalanine | − |
| Resistance to NaCl (7.5%) | − |
| Phosphatase | + |

+: Positive −: Negative

TABLE 8

Chemotaxonomic Properties

| 1) | Cellular lipids | |
|---|---|---|
| | •Ubiquinone | Negative |
| | •Menaquinone | MK-7 |

TABLE 8-continued

Chemotaxonomic Properties

| 2) | Diamino acid composition of cell wall peptidoglycan | meso-$A_2$ pm |
|---|---|---|

The strains having the bacteriological properties mentioned above were compared with the strains indicated in Bergey's Manual of Systematic Bacteriology (Vol. 2, 1986).

Both the strains TH2 and TH3 are classified to the genus Bacillus of bacteria. The strains TH2 and TH3 were identified as Bacillus sp. TH2 and Bacillus sp. TH3, respectively. These strains have been deposited with the National Institute of Bioscience and Human-Technology, Agency of Industrial Science and Technology in Japan as of Sep. 1, 1993 under FERM BP-4397 for the strain TH2 and under FERM BP-4398 for the strain TH3, both under the terms of the Budapest Treaty.

The medium for cultivating these microorganisms may be any of natural media and synthetic media, so long as it contains carbon sources, nitrogen sources, inorganic salts, etc. that may be assimilated by microorganisms having an activity of catalyzing the hydroxylation of L-proline to produce cis-3-hydroxy-L-proline.

As the carbon sources, carbohydrates such as glucose, fructose, sucrose, molasses containing these compounds, starch and starch hydrolysates, etc.; organic acids such as acetic acid, propionic acid, etc.; alcohols such as ethanol, propanol, etc. may be used.

As the nitrogen sources, ammonia; ammonium salts of various inorganic and organic acids such as ammonium chloride, ammonium sulfate, ammonium acetate, and ammonium phosphate, etc.; other nitrogen-containing compounds; peptone, meat extracts, yeast extracts, corn steep liquor, casein hydrolysates, soy bean cakes, soy bean cake hydrolysates, various cultured cells of microorganisms, their digested products, etc. may be used.

The inorganic material includes, for example, potassium dihydrogen phosphate, dipotassium hydrogen phosphate, magnesium phosphate, magnesium sulfate, sodium chloride, ferrous sulfate, manganese sulfate, copper sulfate, and calcium carbonate, etc.

The cultivation of these microorganisms is carried out under aerobic conditions, for example, by shaking culture or by submerged-aerial stirring culture. The temperature for the cultivation is preferably from 15 to 37° C., and the period for the cultivation is generally from 16 to 96 hours. During cultivation, the pH of the medium is kept at 5.0 to 9.0 with inorganic or organic acids, alkaline solutions, urea, calcium carbonate, ammonia, etc.

The thus-cultivated microorganisms can be used as the enzyme source in the process for producing cis-3-hydroxy-L-proline. The amount of enzyme source to be used in the process for producing cis-3-hydroxy-L-proline depends on the amount of substrate used in the process. Usually, it may be from 1.0 to 10,000,000 U, preferably from 1,000 to 3,000,000 U /liter of the aqueous medium.

In the case of using microbial cells and products obtained by processing microbial cells, the concentration of wet cells be used may generally from 1 to 300 g/l.

The enzyme activity for producing one nmol of cis-3-hydroxy-L-proline for one minute under the conditions mentioned below is defined as one unit (U).

The enzyme preparation to be determined is added to 100 mM TES buffer (pH 7.0) containing 5 mM L-proline, 5 mM 2-ketoglutaric acid, 1 mM ferrous sulfate and 5 mM L-ascorbic acid to make 100 μl in total, and the mixture was allowed to stand at 35° C. for 10 minutes. The reaction mixture is heated at 100° C. for 2 minutes so as to stop the reaction, and the amount of cis-3-hydroxy-L-proline produced in the reaction mixture is determined by high performance liquid chromatography (hereinafter referred to as HPLC).

For the determination, any method capable of determining the amount of cis-3-hydroxy-L-proline may be employed. For instance, generally a post-column derivatization method where HPLC is utilized, and a pre-column derivatization method where the compound to be determined in the reaction mixture is previously reacted with 7-chloro-4-nitrobenz-2-oxa-1,3-diazole (hereinafter referred to as NBD) to form its NBD-derivative, derivative may be used is separated by reversed-phase chromatography using HPLC and the thus-separated derivative is quantitatively determined by spectrofluorometry (excitation wavelength: 503 nm, emission wavelength: 541 nm). The pre-column derivatization method may be conducted, according to the method of William J. Lindblad & Robert F. Diegelmann, et al. [see Analytical Biochemistry, 138, 390–395 (1984)].

The concentration of L-proline used in the process for producing cis-3-hydroxy-L-proline may be from 1 mM to 2M.

The process for producing cis-3-hydroxy-L-proline requires a divalent iron ion. The concentration of the divalent iron ion may generally be from 1 to 100 mM. Any divalent iron ion may be used so long as it does not inhibit the enzyme reaction. For instance, sulfides such as ferrous sulfate, chlorides such as ferrous chloride, ferrous carbonate, the salts of organic acids such as citrates, lactates, fumarates may be used.

The process also requires 2-ketoglutaric acid. The concentration of 2-ketoglutaric acid is generally from 1 mM to 2M. 2-Ketoglutaric acid itself may be added to the aqueous medium, or alternatively, the compound that may be converted into 2-ketoglutaric acid by the metabolic activity of the microorganism used in the enzymatic reaction may be added thereto. The compound includes, for example, saccharides such as glucose, glutamic acid and succinic acid. These compounds may be used singly or in combination.

The aqueous medium to be used in the process for producing cis-3-hydroxy-L-proline includes, for example, water, buffers such as phosphates, carbonates, acetates, borates, citrates, tris-buffers, alcohols such as methanol and ethanol, esters such as ethyl acetate, ketones such as acetone, and amides such as acetamide.

The enzymatic reaction may be carried out in the culture medium where the above-mentioned microorganisms having an activity of catalyzing hydroxylation of L-proline to produce cis-3-hydroxy-L-proline are being cultivated or have been cultivated, or alternatively, the enzymatic reaction may also be carried out in an aqueous medium containing the cells of the above-mentioned microorganisms separated from the culture, processed cells, or a purified or crude enzyme derived from the cells.

Processed cells of the microorganisms include, for example, dried cells, lyophilized cells, surfactant-treated cells, enzymatically-treated cells, ultrasonically-treated cells, mechanically-ground cells, mechanically-compressed cells, solvent-treated cells, fractionated cell proteins, immobilized cells, immobilized materials obtained by processing their cells, etc.

The enzymatic reaction is generally carried out at a temperature of 15 to 5° C. and at a pH of 6.0 to 9.0, for a period of 1 to 96 hours. If desired, surfactants and/or organic solvents may be added during the processing of the cells or during the enzymatic reaction.

As the surfactants, mention may be made of cationic surfactants such as polyoxyethylene-stearylamine (e.g., Nymeen S-215, produced by Nippon Oils and Fats Co.), cetyltrimethylammonium bromide, Cation FB and Cation F2-40E, etc.; anionic surfactants such as sodium oleylamidosulfate, Newrex TAB and Rapizole 80; ampholytic surfactants such as polyoxyethylene-sorbitan monostearate (e.g., Nonion ST221); other tertiary amines PB, hexadecyldimethylamine, etc. Any surfactant that may promote the reaction may be employed. The concentration of the surfactant to be employed in the reaction may be generally from 0.1 to 50 mg/ml, preferably from 1 to 20 mg/ml.

As the organic solvent, mention may be made of toluene, xylene, aliphatic alcohols, benzene, ethyl acetates etc. Generally, the concentration of the solvent in the process may be from 0.1 to 50 μl/ml, preferably from 1 to 20 μl/ml.

To recover cis-3-hydroxy-L-proline from the aqueous medium, ordinary separation methods such as column chromatography using ion-exchange resins, crystallization, etc. may be employed. The structure of the recovered cis-3-hydroxy-L-proline may be identified by ordinary analytical methods such as $^{13}$C-NMR spectrum $^1$H-NMR spectrum, mass spectrum, specific rotation or the like.

Next, the novel enzyme, the L-proline-3-hydroxylase of the present invention is described below.

The L-proline-3-hydroxylase may be obtained by cultivating a microorganism having an ability to produce L-proline-3-hydroxylase in a medium so as to produce and accumulate the L-proline-3-hydroxylase in the culture medium, and recovering the L-proline-3-hydroxylase from the culture.

Any microorganisms having an ability to produce L-proline-3-hydroxylase may be employed. For example, microorganisms belonging to the genus Streptomyces or Bacillus and having such activity can be used. Specific examples are *Streptomyces canus* ATCC12647, *Streptomyces canus* ATCC12646, Streptomyces sp. TH1, Bacillus sp. TH2 and Bacillus sp. TH3, a sub-cultivated strain thereof, its mutant thereof, its derivative thereof, etc.

The medium for cultivating these microorganisms may be any of natural media and synthetic media, so long as the media contains carbon sources, nitrogen sources, inorganic salts, etc. that may be assimilated by microorganisms having an ability to produce L-proline-4-hydroxylase.

The carbon source includes, for example, carbohydrates such as glucose, fructose, sucrose, molasses containing these components, starch and starch hydrolysates; organic acids such as acetic acid and propionic acid; alcohols such as ethanol and propanol which may be assimilated by the microorganisms.

As the nitrogen source, ammonia; ammonium salts of various inorganic acids and organic acids such as ammonium chloride, ammonium sulfate, ammonium acetate and ammonium phosphate; other nitrogen-containing compounds; peptone, meat extracts, yeast extracts, corn steep liquor, casein hydrolysates, soy bean cakes, soy bean cake hydrolysates, various microorganisms for fermentation, their digested products, etc. may be used.

As the inorganic material, dipotassium hydrogen phosphate, potassium dihydrogen phosphate, magnesium phosphate, magnesium sulfate, sodium chloride, ferrous sulfate, manganese sulfate, copper sulfate, calcium carbonate, etc. can be used.

The cultivation of these microorganisms is carried out under aerobic conditions, for example, with shaking culture or submerged-aerial stirring culture. The temperature for the cultivation is preferably from 15 to 37° C., and the period for the cultivation is generally from 16 to 96 hours.

During the cultivation, the pH of the medium is kept at 5.0 to 9.0 with inorganic or organic acids, alkaline solutions, urea, calcium carbonate, ammonia, etc. During the cultivation, L-proline may be added, if desired.

To isolate and purify the enzyme from the culture containing the enzyme, any ordinary method for isolating and purifying an enzyme may be employed. For instance, the culture is subjected to centrifugation to collect the cultivated cells therefrom, and the cells are fully washed and then disrupted by an ultrasonic cell disrupter, a French press, a Manton-Gauline homogenizer, a Dyno mill, etc. to obtain a cell-free extract. The cell-free extract is again subjected to centrifugation, and the enzyme in the resulting supernatant is then purified, for example, by salting-out with ammonium sulfate or the like, by anion-exchange chromatography with diethylaminoethyl (DEAE)-Sepharose or the like, by hydrophobic chromatography with butyl-Sepharose, phenyl-Sepharose or the like, by dye affinity chromatography with red-Agarose or the like, by gel filtration with molecular sieves or by electrophoresis such as isoelectric point electrophoresis or the like. In this way, a pure product of the enzyme is obtained. The activity of the L-proline-3-hydroxylase thus isolated may be determined by the same method as mentioned above.

The L-proline-3-hydroxylase, thus obtained according to the manner mentioned above, has the following physicochemical properties (1) to (11):

(1) Action and Substrate Specificity

The enzyme catalyzes the hydroxylation of L-proline at the 3-position of L-proline in the presence of 2-ketoglutaric acid and a divalent iron ion to produce cis-3-hydroxy-L-proline.

(2) Optimum pH Range

The enzyme has an optimum pH range of 6.5 to 7.5 for its reaction at 30° C. for 20 minutes.

(3) Stable pH Range

The enzyme is stable at pH values ranging from 6.5 to 8.0, when it is allowed to stand at 4° C. for 23 hours.

(4) Optimum Temperature Range

The optimum temperature range is in 35 to 40° C., when it is allowed to stand at pH 7.0 for 15 minutes.

(5) Stable Temperature Range

The enzyme is inactivated, when it is allowed to stand at pH 7.5 and at 50° C. for 30 minutes.

(6) Inhibitors

The activity of the enzyme is inhibited by metal ions of $Zn^{++}$, $Cu^{++}$, $Co^{++}$ and $Ba^{++}$ and ethylenediaminetetraacetic acid (EDTA).

(7) Activation

The enzyme does not need any cofactor for its activation. L-Ascorbic acid accelerates the activity of the enzyme.

(8) Km Value

The Km value is 0.49 mM for L-proline and is 0.11 mM for 2-ketoglutaric acid, when determined in a 100 mM N-tris(hydroxymethyl)methyl-2-aminoethanesulfonic acid (TES) buffer (pH7.0) containing 5mM L-ascorbic acid, 1 mM ferrous sulfate and a pre-determined amount of this enzyme.

(9) Isoelectric Point

The enzyme has an isoelectric point of 4.3 as determined by Phast system.

(10) Molecular Weight

The enzyme has a molecular weight of 35,000±5,000 daltons by sodium dodecylsulfate-polyacrylamide gel electrophoresis.

(11) N-terminal Amino Acid Sequence

The enzyme has an N-terminal amino acid sequence illustrated by Sequence No. 5.

Sequence No. 5
(N-terminal)
1 MetArgSerHisIleLeuGlyArgIleGlu
11 LeuAspGlnGluArgLeuGlyArgAspLeu
21 GluTyrLeuAlaThrValProThrVal The L-proline-3-hydroxylases of the present invention are enzymes which hydroxylate free L-proline in the presence of 2-ketoglutaric acid and divalent iron ions to produce cis-3-hydroxy-L-proline.

The present invention encompasses any and every protein having the enzymatic activity of hydroxylating the 3-position of L-proline, which includes, for example, a protein having the amino acid sequence indicated by Sequence NOs: 1 or 2, a fused protein having an amino acid sequence that results from the protein or a protein having a partial amino acid sequence of the protein as bonded to a peptide having a partial amino acid sequence of an *Escherichia coli*-derived β-galactosidase protein, a fused protein having an amino acid sequence that results from the protein having the amino acid sequence indicated by Sequence NO: 1 or 2 or a protein having a partial amino acid sequence of the protein as bonded to a peptide having a partial amino acid sequence of an *E. coli*-derived maltose-binding protein, etc. Examples of the fused proteins include proteins having the amino acid sequence as indicated by Sequence NO: 15, 16 or 17, etc.

The amino acid sequence indicated by Sequence NO: 1, 2, 15, 16 or 17 includes proteins having an amino acid sequence with one or more amino acids substituted, deleted or added and having the enzymatic activity of hydroxylating the 3-position of L-proline. The substitution, the deletion and the addition of amino acids can be conducted in accordance with the methods described in Nucleic Acids Research, Vol. 10, pp. 6487–6500 (1982); Proc. Natl. Acad. Sci., USA, Vol. 79, pp. 6409–6413 (1982); Proc. Natl. Acad. Sci., USA, Vol.81, pp. 5662–5666 (1984); Science, Vol.224, pp. 1431–1433 (1984); PCTWO85/00817 (1985); Nature, Vol.316, pp. 601–605 (1985); Gene, Vol. 34, pp. 315–323 (1985); Nucleic Acids Research, Vol. 13, pp. 4431–4442 (1985); Current Protocols in Molecular Biology, Chap. 8, Mutagenesis of Cloned DNA, John Wiley & Sons, Inc. (1989), etc.

The present invention encompasses any and every L-proline-3-hydroxylase genes of a DNA fragment containing a gene that codes for a protein having the enzymatic activity of hydroxylating the 3-position of L-proline, and this may include, for example, genes coding for the protein having the amino acid sequence as indicated by Sequence NO: 1, 2, 15, 16, or 17, and also genes which code for a protein that has an amino acid sequence corresponding to the amino acid sequence as indicated by SEQ ID NO: 1, 2, 15, 16 or 17 and derived therefrom by substitution, deletion or addition of at least one amino acid and which have the enzymatic activity of hydroxylating the 3-position of L-proline. Concretely mentioned are DNAs indicated by Sequence NOs: 3, 4, 13 and 14.

The L-proline-3-hydroxylases genes of the present invention include the DNAs as defined hereinabove and also DNAs as derived therefrom by mutation, such as substituting mutation, deleting mutation, inserting mutation or the like, to be conducted to the extent that the mutated DNAs do not lose the L-proline-3-hydroxylases activity, for example, DNAs with homology to SEQ ID NO: 3, 4, 13 or 14. Such homologous DNAs are those to be obtained by colony hybridization or plaque hybridization using, as a probe, the DNA having the nucleotide sequence as indicated by SEQ ID NO: 3, 4, 13 or 14. These treatments can be conducted in accordance with known in vitro recombination techniques [see Molecular Cloning: A Laboratory Manual, 2nd Ed., edited by Sambrook, Fritsch, Maniatis, published by Cold Spring Harbor Laboratory Press, 1989].

DNA fragments containing the L-proline-3-hydroxylases gene can be obtained from microorganisms having the ability of hydroxylating L-proline to produce cis-3-hydroxy-L-proline. As the microorganisms, any microorganism having the ability of hydroxylating L-proline to produce cis-3-hydroxy-L-proline can be employed in the present invention. A preferred example of such a microorganism, are microorganisms belonging to the genus Streptomyces or Bacillus and having the enzymatic activity of hydroxylating the 3-position of L-proline can be mentioned. More preferable examples thereof include *Streptomyces canus* ATCC12647, *Streptomyces canus* ATCC12646, Streptomyces sp. TH1 (FERM BP-4399), Bacillus sp. TH2 (FERM BP-4397), Bacillus sp. TH3 (FERM BP-4398), or mutants or derivatives of these strains.

Methods for obtaining L-proline-3-hydroxylases genes derived from microorganisms having the ability of producing L-proline-3-hydroxylases are described below.

Chromosomal DNA is prepared from a microorganism having the ability to produce L-proline-3-hydroxylase through a usual DNA isolation method, for example, a phenol method [see Biochem. Biophys. Acta, 72, 619–629 (1963)]. The thus-obtained chromosomal DNA is cleaved with suitable restriction enzymes, then the resulting fragments are inserted into vector DNAs to construct chromosomal DNA libraries for the chromosomes of the microorganisms. Using the chromosomal DNA library, host microorganisms can be transformed. The transformants containing the L-proline-3-hydroxylase gene are selected from the obtained transformants by hybridization method. DNAs containing the intended gene can be obtained from the thus-selected transformants.

The process comprising a series of such steps can be conducted in accordance with known in vitro recombination method (molecular Cloning, A Laboratory Manual, 2nd edition, edited by Sambrook, Fritsch and Maniatis, Cold Spring Harbor Laboratory Press, 1989).

As the vector DNAs that are used to construct the chromosomal DNA library of the microorganism having the ability of producing L-proline-3-hydroxylase, phage vectors and plasmid vectors can be used if they can be replicated autonomously in *Escherichia coli* K12 strain. Preferable examples of the vector DNA include λZAPII, pUC18 and pBluescript (commercially available from STRATAGENE Co.).

As the host microorganisms that are used to construct the chromosomal DNA library of the microorganism having the ability of producing L-proline-3-hydroxylase, any of the microorganisms belonging to the genus Escherichia can be used. Preferable examples of the host microorganisms include *E. coli* XL1-Blue, *E. coli* XL2-Blue, *E. coli* DH1, *E. coli* MC1000,etc.

Based on information obtained from the amino acid sequence of L-proline-3-hydroxylase, DNA primers are synthesized. Using the DNA primers, DNA fragments are prepared through polymerase chain reaction (hereinafter referred to as PCR) . Using the thus-obtained DNA fragments, transformants containing an L-proline-3-hydroxylase gene can be selected by the hybridization method.

Information on the amino acid sequences of L-proline-3-hydroxylases can be obtained through analysis of pure L-proline-3-hydroxylases using ordinary amino acid sequencers, such as Protein Sequencer Model PPSQ-10 (produced by Shimadzu Seisakusho K.K.). As the information on the amino acid sequences thus obtained, concretely mentioned are the amino acid sequences as indicated by Sequence Nos. 5 to 7, etc.

The DNA primers can be synthesized by means of ordinary DNA synthesizers, for example, a 380A.DNA Synthesizer (produced by Applied Biosystems Co.), etc.

Probes for hybridization, which may be used are partial fragments of L-proline-3-hydroxylases genes, which can be obtained through PCR. For example, a DNA as indicated by Sequence NO: 8 in the Sequence List (this corresponds to a sense chain DNA coding for from the first to the sixth amino acids in the amino acid sequence of SEQ ID NO: 1) and a DNA as indicated by Sequence No. 10 in the Sequence List (this corresponds to an anti-sense chain DNA coding for from the 21st to 25th amino acids in the amino acid sequence of Sequence No. 1) are chemically synthesized. Through PCR using these partial fragment as DNA primers, obtained is a DNA fragment of 74 bp as indicated by SEQ ID NO: 11 is obtained. The thus-obtained DNA fragment can be used as probe for hybridization.

The DNA which is obtained from the transformant as selected through hybridization and which contains an L-proline-3-hydroxylases gene, is cleaved with suitable restriction enzymes, such as PstI or the like, and then cloned into plasmids, such as pBluescript KS(+) (commercially available from STRATAGENE Co.). The nucleotide sequence of the above-mentioned gene can be determined by ordinary base sequencing methods, such as the dideoxy chain termination method of Sanger et al[see Proc. Natl. Acad. Sci., USA, 74, 5463 (1977)]. The determination of the nucleotide sequence can be conducted using automatic DNA sequencers, such as 373A.DNA Sequencer (produced by Applied Biosystems Co.) or the like.

As the thus-determined nucleotide sequences of L-proline-3-hydroxylases genes, for example the nucleotide sequences as indicated by SEQ ID NOs: 3, 4, 13 and 14.

The DNA that codes for an L-proline-3-hydroxylase of the present invention can be introduced into vectors in a usual manner. As the vectors containing the DNA that codes for an L-proline-3-hydroxylases of the present invention, for example, pTH30, pTH71, pTH75, etc. can be mentioned. *Escherichia coli* XL2-Blue/pTH30 which is *Escherichia coli* containing pTH30 and *Escherichia coli* XL2-Blue/pTH75 which is *Escherichia coli* containing pTH75 were deposited at the National Institute of Bioscience and Human-Technology of the Agency of Industrial Science and Technology (which is located at 1-3, Higashi 1-chome, Tsukuba-shi, Ibaragi-ken 305, Japan) as of Mar. 2, 1995 under FERM BP-5026 for the strain XL2-Blue/pTH30 and as of Feb. 22, 1996 under FERM BP-55409 for the strainin XL2-Blue/pTH75, both under the terms of the Budapest Treaty.

To express the thus-obtained L-proline-3-hydroxylase genes in hosts, the DNA fragment containing the L-proline-3-hydroxylase gene is first cleaved with a restriction enzyme or deoxyribonucleases (DNases) to form a DNA fragment of a suitable length containing the L-proline-3-hydroxylases gene. The thus-formed DNA fragment is inserted into an expression vector at the downstream position of the promoter therein, and thereafter the expression vector having the thus-inserted DNA therein is introduced into a host cell suitable for the expression vector.

As the host, usable is any one capable of being expressed in the intended gene. For example, the host includes microorganisms belonging to the genus Escherichia, Serratia, Corynebacterium, Brevibacterium, Pseudomonas, Bacillus, etc., as well as yeast strains, animal cell hosts, etc.

As the expression vector, one which is autonomously replicable in the above-mentioned hosts or capable of being inserted into their chromosomes and which contains a promoter at the position at which the L-proline-3-hydroxylases gene can be transcribed, may be used.

When microorganisms such as *Escherichia coli* or the like are used as the host, it is desirable that the L-proline-3-hydroxylases expression vector is replicated autonomously in the microorganisms and is composed of a promoter, a ribosome-bonding sequence, an L-proline-3-hydroxylase gene and a transcription terminator sequence. A regulatory gene may be contained therein.

As examples of the expression vector, mentioned are pBTrp2, pBTac1, pBTac2 (all commercially available from Boehringer Mannheim Co.); pKYP10 (see Japanese Published Unexamined Patent Application No. 58-110600); pKYP200 [see Agric. Biol. Chem., Vol. 48, pp. 669–675 (1984)]; pLSA1 [see Agric. Biol. Chem., Vol. 53, p. 277 (1989)]; pGEL1 [see Proc. Natl. Acad. Sci., USA, Vol. 82, p. 4306 (1985)]; pBluescript (produced by STRATAGENE Co.); pTrs30 [prepared from *Escherichia coli* JM109/pTrS30 (FERM BP-5407); pTrs32 [prepared from *Escherichia coli* JM109/pTrs32 (FERM BP-5408)], etc.

As the promoter, usable is any one capable of being expressed in hosts such as *Escherichia coli*, etc. For example, mentioned are promoters derived from *Escherichia coli*, phage, etc., such as trp promoter (Ptrp), lac promoter (Plac), $P_L$ promoter and $P_R$ promoter. Also usable are artificially designed and modified promoters, such as Ptrpx2 to be prepared by connecting two Ptrp's in series, as well as tac promoter.

As the ribosome-bonding sequence, any one capable of being expressed in hosts such as *Escherichia coli*. can be used. However, it is desirable to use plasmids having a ribosome-bonding sequence and an initiation codon as spaced at suitable intervals therebetween (for example, by from 6 to 18 bases).

The L-proline-3-hydroxylase gene may be any and every gene that codes for an L-proline-3-hydroxylase. However, it is desirable that the bases constituting the DNA sequence of the gene are suitably substituted in order that the substituted DNA sequence can be constituted of codon most suitable for expression in the host microorganisms to be used.

Transcription terminator sequences are not always necessary for the expression of the genes of the present invention. However, if used it is desirable that a transcription terminator sequence is arranged just after the structural gene.

Examples of the hosts usable in the present invention include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Bacillus subtilis, Bacillus amyloliquefacines, Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium acetoacidophilum* ATCC13870, *Microbacterium ammoniaphilum* ATCC15354, etc.

When yeast strains are used as the host, for example, YEp13 (ATCC37155), YEp24 (ATCC37051), YCp50 (ATCC37419), etc. can be used as the expression vector.

As the promoter, any one that can be expressed in the host of yeast strains can be used. For example, promoters in genes of glycolases, such as hexosekinase, etc., as well as other promoters such as gal 1 promoter, gal 10 promoter, heat-shock protein promoters, MF α1 promoter, CUP 1 promoter, etc, may be used.

As examples of host cells, *Saccharomyces cerevisae*, Schizosaccharomyces probe, *Kluyveromyces lactis, Trichosporon pullulans, Schwanniomyces alluvius*, etc. can be mentioned.

When animal cells are used as the host, for example, pcDNA I/Amp, pcDNA I, pcDM8 (all commercially available from Funakoshi Co.), etc. can be used as the expression vector. As the promoter, any one that can be expressed in the host of animal cells can be used. For example, usable are promoters such as those in human CMV IE (immediate early) genes. An enhancer of human CMV IE genes can be used along with the promoter.

As examples of the host cells, Namalwa cells, HBT 5637 cells (see Japanese Published Unexamined Patent Application No. 299/88), COS cells, CHO cells, etc. can be used.

To introduce DNA into animal cells, any and every method capable of introducing DNA into animal cells can be employed herein. For example, employable are electroporation methods [see Miyaji et al., Cytotechnology, 3, 133 (1990)], calcium phosphate methods (see Japanese Published Unexamined Patent Application No. 227075/90), lipofection methods [see Philip L. Felgner, et al., Proc. Natl. Acad. Sci., USA, 84, 7413 (1987)], etc. The resulting transformants can be collected and cultivated in accordance with the methods described in Japanese Published Unexamined Patent Application Nos. 227075/90 and 257891/90.

The transformants obtained in the manner mentioned above can be cultivated according to ordinary incubation methods.

As the media for cultivating the transformants obtained by using the hosts of microorganisms such as *Escherichia coli*, yeast strains, etc., both natural and synthetic media can be employed so long as the media properly contain carbon sources, nitrogen sources, inorganic salts and other materials capable of being assimilated by the microbial hosts and in which the transformants can be efficiently cultivated.

Any carbon sources that can be assimilated by the microorganisms may be used. Examples of the carbon source include carbohydrates such as glucose, fructose, sucrose, molasses containing these components, starch and starch hydrolyzates; organic acids such as acetic acid and propionic acid; and alcohols such as ethanol and propanol.

As the nitrogen sources, ammonia, ammonium salts of inorganic and organic acids such as ammonium chloride, ammonium sulfate, ammonium acetate and ammonium phosphate, other nitrogen-containing compounds, peptone, meat extracts, yeast extracts, corn steep liquor, casein hydrolyzates, soybean cakes, soybean cake hydrolyzates, cultured fermented cells, their digested products, etc. may be used.

As inorganic salts, potassium dihydrogen phosphate, dipotassium hydrogen phosphate, magnesium phosphate, magnesium sulfate, sodium chloride, ferrous sulfate, manganese sulfate, copper sulfate, calcium carbonate, etc. may be used.

The cultivation is conducted under aerobic conditions, for example, with shaking culture or submerged-aerial stirring culture. The temperature for the cultivation is 15 to 40° C. The period for the cultivation is usually 16 to 96 hours. During the cultivation, the pH of the medium is kept at 3.0 to 9.0. The pH is adjusted using inorganic or organic acids, alkaline solutions, urea, calcium carbonate, ammonia or the like.

L-Proline is suitably added to the media in such a manner that its concentration may be from 5 to 1000 mM, preferably from 20 to 200 mM, whereby the intended L-proline-3-hydroxylases can be produced more efficiently.

Antibiotics such as ampicillin, tetracycline or the like may be added to the medium during the cultivation, if required.

For the cultivation of the microorganisms which are transformed with the expression vector using the inducible promoter, inducers may be added to the medium, if required. For example, in cultivation of microorganisms transformed with an expression vector using lac promoter, isopropyl-B-D-thiogalactopyraNos.ide (IPTG) maybe added to the medium. In cultivation of microorganisms transformed with an expression vector using trp promoter, indoleacrylic acid (IAA) may be added to the medium.

As the medium for cultivating the transformants which are obtained using animal cells as a host cell, RPMI1640 medium and Eagle's MEM medium, which are generally used or these culture media containing a fetal bovine serum, can be used.

The cultivation of the cells is conducted in the presence of 5% $CO_2$. The temperature for the cultivation is preferably 35 to 37° C., and the period for the cultivation is usually 3 to 7 days.

L-Proline is suitably added to the media in such a manner that its concentration may be from 5 to 1000 mM, preferably from 20 to 200 mM, whereby the intended L-proline-3-hydroxylases can be produced more efficiently.

Antibiotics such as kanamycin, penicillin or the like may be added to the medium during the cultivation, if required.

A considerable amount of L-proline-3-hydroxylase is produced and accumulated in the thus-cultivated transformants in comparison to the microorganism strain used as the gene source, such as Streptomyces sp. TH1 or the like. Thus, the isolation and purification of the enzyme or the production of cis-3-hydroxy-L-proline from L-proline using the enzyme can be performed far more efficiently in comparison to the production of cis-3-hydroxy-L-proline from L-proline using the non genetically-engineered microorganism as the enzyme source, such as Streptomyces sp. TH1 or the like.

The production of L-proline-3-hydroxylase in the transformants can be carried out by adding the culture, the cells or the treated cells to an aqueous medium suitable for the enzymatic reaction together with L-proline, a divalent iron ion and 2-ketoglutaric acid, and adding a surfactant or an organic solvent, if required, to determine cis-3-hydroxy-L-proline produced. With respect to the activity of the L-proline-3-hydroxylase of which the formation is confirmed in the cell, the activity of the enzyme for producing 1 nmol of cis-3-hydroxy-L-proline for 1 minute under the following conditions is defined as 1 unit (U). The microorganism cells and the animal cells are here called cells.

Measurement of L-proline-3-hydroxylase Activity

The cells, the treated cells or the enzyme preparation are added to 240 mM TES [N-tris(hydroxymethyl)methyl-2-aminoethanesulfonic acid] buffer containing 12 mM L-proline, 24 mM 2-ketoglutaric acid, 4 mM ferrous sulfate and 8 mM L-ascorbic acid to make 250 μl in total. The mixture is kept at 35° C. for 10 minutes. The reaction mixture is heated at 100° C. for 2 minutes to stop the reaction, and the amount of cis-3-hydroxy-L-proline produced in the reaction mixture is determined by HPLC.

For the determination, any method capable of determining the amount of cis-3-hydroxy-L-proline may be employed. For instance, generally usable are (1) a post-column derivatization method and (2) a pre-column derivatization method as mentioned above.

The enzyme may be isolated and purified in a usual manner from culture of the transformant in which the formation of L-proline-3-hydroxylase is confirmed in the cultivated cell as mentioned above. For instance, the culture broth of the transformant is centrifuged to collect the cultivated cells therefrom, and the cells are washed and then disrupted by an ultrasonic cell disrupter, a French press, a Manton-Gauline homogenizer, a Dyno mill or the like to obtain a cell-free extract. The purified enzyme preparation can be obtained by ammonium sulfate precipitation, anion exchange chromatography such as diethylaminoethyl (DEAE) Sepharose or the like, hydrophobic chromatography such as butyl-Sepharose, phenyl-Sepharose or the like, gel filtration, electrophoresis such as isoelectric point electrophoresis, etc., from the supernatant of the cell-free extract obtained by centrifugation.

The cultivated transformant cells that have been identified to contain the L-proline-3-hydroxylase as formed therein can be cultivated under the same conditions as above, under which the transformant was cultivated, to thereby make the cells produce and accumulate cis-3-hydroxy-L-proline in the cells, and the thus-produced cis-3-hydroxy-L-proline can be collected from the culture to obtain it.

If the transformant cells derived from host cells which have the ability of producing L-proline from saccharide sources and accumulating it in the cultures and where such cells are used, it is possible to produce cis-3-hydroxy-L-proline even if L-proline is not added to the media during the cultivation of the cells therein. However, it is desirable to suitably add to the media L-proline at a concentration of from 5 to 1000 mM, preferably from 20 to 200 mM, whereby the intended L-proline-3-hydroxylases can be produced more efficiently.

If the transformant cells have the ability to produce 2-ketoglutaric acid from saccharide sources and accumulating it in the cultures and where such cells are used, it is possible to produce cis-3-hydroxy-L-proline even if 2-ketoglutaric acid is not added to the media during the cultivation of the cells therein. Where such transformant cells are used, saccharide sources such as glucose, etc. may be suitably added to the media to make the cells produce and accumulate 2-ketoglutaric acid in the cultures, whereby the intended L-proline-3-hydroxylases can be produced more efficiently. Where, on the other hand, transformant cells not having the ability of producing 2-ketoglutaric acid from saccharide sources are used, 2-ketoglutaric acid may be added to the media during the cultivation of the cells, if desired.

If desired, 2-ketoglutaric acid and divalent iron ions may be added to the media during the cultivation of the transformant cells.

To produce cis-3-hydroxy-L-proline an alternative method may be used as mentioned below, which uses, as the enzyme source, cultures of the transformant cells where the formation of L-proline-3-hydroxylases has been identified, cells isolated from the cultures, or the products as obtained by processing the cells.

The alternative method of producing cis-3-hydroxy-L-proline is as follows:

The cultures of the transformant cells, the cells isolated from the culture, or the products as obtained by processing the cells are added to aqueous media suitable for enzymatic reaction, along with L-proline, divalent iron ions and 2-ketoglutaric acid and optionally with surfactants and organic solvents, thereby converting L-proline into cis-3-hydroxy-L-proline, and thereafter the resulting cis-3-hydroxy-L-proline is collected from the reaction mixtures.

As examples of the processed cells, dried cells, lyophilized cells, surfactant-treated cells, enzymatically-treated cells, ultrasonically-treated cells, mechanically-ground cells, mechanically-compressed cells, solvent-treated cells, fractionated cell proteins, immobilized cells, immobilized materials obtained by processing their cells, etc. can be used. The enzymes preparation obtained by extraction from the cells having L-proline-3-hydroxylase activity, purified products of these enzymes, and immobilized products thereof can also be used.

As examples of the aqueous medium, water, buffers such as phosphates, carbonates, acetates, borates, citrates and tris-buffers, alcohols such as methanol and ethanol, esters such as ethyl acetate, ketones such as acetone, and amides such as acetamide, can be mentioned.

As examples of the surfactant, cationic surfactants such as polyoxyethylene-stearylamine (for example, Nymeen S215 produced by Nippon Oils & Fats Co.), cetyltrimethylammonium bromide, Cation FB, Cation F2-40E, etc.; anionic surfactants such as sodium oleylamidosulfate, Newrex TAB, and Rapizole 80; ampholytic surfactants such as polyoxyethylene-sorbitan monostearate (for example, Nonion ST221) or the like; and also other tertiary amines PB, hexadecyldimethylamine, etc. can be mentioned. Any and every surfactant that promotes the reaction may be employed. The concentration of the surfactant is usually from 0.1 to 50 mg/liter, preferably from 1 to 20 mg/liter.

As examples of the organic solvent, toluene, xylene, aliphatic alcohols, benzene and ethyl acetate can be mentioned. The concentration of the organic solvent is usually from 0.1 to 50 $\mu$l/ml, preferably from 1 to 20 $\mu$l/ml.

The reaction may be conducted during the cultivation of the transformant having the activity of L-proline-3-hydroxylase, or may also be conducted after the completion of the cultivation, in the aqueous medium using the cells, the treated cells, the purified enzyme or the crude enzyme prepared from the culture.

The amount of the enzyme added to the reaction mixture is determined depending on the amount of the substrate used. It is usually from 1.0 to 10,000,000 U/liter, preferably from 1,000 to 3,000,000 U/liter. In case of using the cells or the treated cells of the microorganism, the concentration of wet cells is usually from 1 to 300 g/liter.

The reaction is usually conducted at a temperature from 15 to 50° C. at a pH from 6.0 to 9.0 for 1 to 96 hours.

The concentration of L-proline used in the reaction may be from 1 mM to 2 M. L-Proline can be supplied by adding L-proline itself to the reaction mixture, or adding the culture of the microorganism which can produce and accumulate L-proline from sugar source. Further, if a microorganism having the ability of producing L-proline from a sugar source is used as the host microorganism of the transformant, L-proline produced from a sugar source by the host microorganism can be used in the reaction. That is, L-proline produced by the transformant derived from the host microorganism having the ability to produce L-proline is converted into cis-3-hydroxy-L-proline in the culture using L-proline-3-hydroxylase produced by the transformant, whereby cis-3-hydroxy-L-proline can be produced in the culture broth without the addition of L-proline.

The divalent iron ion is required for the reaction. This divalent iron ion is ordinarily used in a concentration of from 1 to 100 mM. Any divalent iron ion can be used so long it does not inhibit the reaction. As examples of the divalent iron ion, sulfates such as ferrous sulfate; chlorides such as ferrous chloride; ferrous carbide; and organic acid salts such as citrates, lactates and fumarates can be mentioned. When the divalent iron ion is already present in the cells, the treated cells or the reaction mixture, divalent iron need not be added.

2-Ketoglutaric acid itself may be added to the reaction mixture or may be supplied from a compound which can be converted into 2-ketaglutaric acid by the metabolic activity of the cells or the treated cells used. As examples of such a compound, saccharides such as glucose; amino acids such as glutamic acid; and organic acids such as succinic acid can be mentioned. These compounds may be used singly or in combination.

Cis-3-hydroxy-L-proline is recovered from the culture or the aqueous medium by any ordinary separation method, for example, column chromatography using an ion-exchange resin, etc. by crystallization, etc.

The structure of the thus-recovered cis-3-hydroxy-L-proline can be identified by ordinary analytical method such as $^{13}$C-NMR spectrum, $^1$H-NMR spectrum, mass spectrum, specific rotation or the like.

The cis-3-hydroxy-L-proline produced by the present invention can be determined quantitatively by the above-mentioned post-column derivatization method or pre-column derivatization method.

The present invention is illustrated more specifically by referring to the following Examples.

EXAMPLE 1

(1) Production of Cis-3-hydroxy-L-proline

SR3 medium comprising 1.0% glucose, 1.0% soluble starch, 0.5% yeast extract, 0.5% tryptone, 0.3% meat extract and 0.05% magnesium phosphate, and adjusted to pH 7.2 with 6N NaOH, was put in test tubes (diameter 25 mm×length 200 mm) in an amount of 10 ml each and sterilized at 120° C. for 20 minutes. One loopful of cells of Streptomyces sp. TH1, that had grown in HT-agar plate medium comprising 1% soluble starch, 0.2% NZ amine, 0.1% yeast extract, 0.1% meat extract and 1.5% agar, adjusted to pH 7.2 with 6N NaOH, and sterilized at 120° C. for 20 minutes, was inoculated into the above-mentioned SR3 medium in each test tube and cultivated at 28° C. for 2 days by shaking. The resulting culture was used as the 1st seed culture in the following step.

SR3 medium was put in 2 liter-Erlenmeyer flasks in an amount of 200 ml each and sterilized at 120° C. for 20 minutes. The above-mentioned 1st seed culture was inoculated in the SR3 medium in each Erlenmeyer flask and cultivated at 28° C. for 2 days by shaking. The resulting culture was used as the 2nd seed culture in the following step.

Df3 medium comprising 5% soluble starch, 3% corn steep liquor, 0.05% potassium dihydrogen phosphate, 0.05% magnesium sulfate 7 hydrate and 0.5% calcium carbonate, and adjusted to pH 7.0 with 6N NaOH, was put in 5 liter-jar fermenters in an amount of 2 liters each and sterilized at 120° C. for 20 minutes. The above-mentioned 2nd seed culture was inoculated in the DF3 medium in each jar fermenter under germ-free condition and cultivated under the condition of 700 rpm and 1 vvm, at 28° C. for 2 days. During the cultivation, the pH of the medium was not adjusted. The thus-obtained culture was subjected to centrifugation at 15,000×g for 10 minutes at 4° C. and 75 g of the wet cells thus separated were obtained per liter of the culture. The wet cells were washed with a physiological saline at 4° C. and then recentrifuged. If desired, the thus-obtained wet cells were frozen and stored at –80° C., and the fozen cells were thawed before use.

One gram of the thus-obtained wet cells was suspended in 10 ml of a reaction mixture (a) [prepared by adding 1.4% (v/v) of Nymeen solution (prepared by dissolving 4 g of Nymeen S-215 (produced by Nippon Oils & Fats Co.) in 10 ml of xylene) to 100 mM TES buffer (pH 7.5) containing 5 mM L-proline, 5 mM 2-ketoglutaric acid, 5 M L-ascorbic acid and 1 mM ferrous sulfate] and the mixture was allowed to stand at 30° C. for 5 hours.

After the reaction, the cells were removed from the reaction mixture by centrifugation, and the amount of cis-3-hydroxy-L-proline produced in the supernatant was determined.

The determination was carried out by a post-column derivatization method with NBD by HPLC under the conditions mentioned below. To identify the intended product, the resulting product was eluted from the column and reacted with NBD in the column line to form its NBD-derivative and the derivative was determined by spectrofluorometry.

| Conditions for determination by HPLC | |
|---|---|
| [1] Apparatus used: | |
| High Performance Liquid Chromatography Device | |
| (produced by Shimadzu Seisakusho K.K.) | |
| Chromatopac | CR6A |
| System controller | SCL-6B |
| Autoinjector | SIL-6B |
| Liquid Chromatograph Pump | LC-6A |
| Column Oven | CTO-6A |
| Chemical Reaction Box | CRB-6A |
| Spectrofluorometric Detector | RF-550A |
| [2] Column Used: | |
| SUMCHIRAL OA5000 (diameter 4.5 mm x length 250 mm, produced by Sumika Chemical Analysis Service Limited) | |
| [3] Conditions for Analysis: | |
| 1)  Mobile Phase: aqueous solution of copper sulfate | 1 mM |
| 2)  Flow Rate of Mobile Phase: | 1.0 ml/min |
| 3)  Column Temperature: | 38° C. |
| 4)  Buffer: | 0.3M boric acid buffer(pH 9.6) 25 mM ethylenediaminetetraacetic acid |
| 5)  Flow Rate of Buffer: | 0.2 ml/min |
| 6)  NBD Solution: methanol solution of | 0.5 g/liter |
| 7)  Flow Rate of NBD Solution: | 0.5 ml/min |
| 8)  Reaction Temperature: | 60° C. |
| 9)  Reaction Time: | about 3 min |
| 10) Wavelength for Detection: | |
| excitation wavelength | 503 nm |
| emission wavelength | 541 nm |
| 11) Sample: | 10 µl |

As a result of the determination, it was verified that 910 µM (119 mg/liter) of cis-3-hydroxy-L-proline was produced in the reaction mixture.

(2) Production of Cis-3-hydroxy-L-proline

Df3 medium was put into atest tube in an amount of 10 ml and sterilized at 120° C. for 20minutes. One ml of the 1st seed culture obtained in the same manner as in (1) of Example 1 was inoculated in the Df3 medium under germ-free conditions and cultivated at 28° C. for 2 days by shaking. The resulting culture was centrifuged at 8000 rpm and at 4° C. for 10 minutes. The cells thus separated were suspended in 80 mM TES (N-tris(hydroxymethyl)methyl-2-aminoethanesulfonic acid] buffer (pH 7.5), washed and then recentrifuged to separate the wet cells. One gram of the thus-obtained wet cells was suspended in 10 ml of a reaction mixture (a) and the mixture was allowed to stand at 30° C. for 30 minutes. After the reaction, the cells were removed from the reaction mixture by centrifugation, and the amount of cis-3-hydroxy-L-proline formed in the supernatant was quantitatively determined.

As a result of the determination, it was verified that 1710 nM (224 µg/liter) of cis-3-hydroxy-L-proline was produced in the reaction mixture.

EXAMPLE 2

Purification of Cis-3-hydroxy-L-proline

One hundred grams of the wet cells which were obtained in (1) of Example 1 was suspended in 1 liter of the reaction mixture (a) as described in (1) of Example 1, that had been placed in a 2 liter-beaker. The suspension was allowed to stand at 30° C. for 5 hours with stirring.

After the reaction, the cells were removed from the reaction mixture by centrifugation, and cis-3-hydroxy-L-proline produced in the supernatant were determined by the same method as described in (1) of Example 1.

As a result of the determination, it was verified that 809 µM (106 mg/liter) of cis-3-hydroxy-L-proline was produced in the reaction mixture.

The supernatant separated from the reaction mixture was adjusted to pH 4.5, and passed through a column packed with 200 ml of an ion-exchange resin, Diaion SK1B ($NH^{4+}$ type, produced by Mitsubishi Kasei Co.). The eluted fractions containing cis-3-hydroxy-L-proline was concentrated under reduced pressure and then passed through a column packed with 20 ml of an ion-exchange resin, Diaion PA412 (OH-type, produced by Mitsubishi Kasei Co.). The eluted fraction containing cis-3-hydroxy-L-proline was concentrated under reduced pressure, and adjusted to pH 9.6, and 10 vol. % of o-phthalaldehyde (OPA) solution (0.075 g of OPA/ml ethanol solution) and 2 vol. % of β-mercaptoethanol solution (10% v/v aqueous solution) were added thereto. The mixture was then allowed to stand at 60° C. for 5minutes, whereby impurities of primary amino acids contained therein were reacted with OPA. The resulting mixture was passed through a column packed with 10 ml of Sepabeads SP207 (produced by Mitsubishi Kasei Co.), to separate cis-3-hydroxy-L-proline from the impurities of OPA-derivatized primary amino acids. The elued fraction containing cis-3-hydroxy-L-proline was concentrated under reduced pressure and again passed through a column packed with 20 ml of an ion-exchange resin, Diaion PA412 (OH-type, produced by Mitsubishi Kasei Co.) to separate a fraction containing cis-3-hydroxy-L-proline. The final fraction was concentrated and dried to obtain 68 mg of cis-3-hydroxy-L-proline as white crystals. The yield of the product was 63%.

Physicochemical properties of the thus-obtained chemical compound were given below.

Specific rotation: $[\alpha]_D^{21} = -93.4$ (c=0.503, $H_2O$)

FAB-mass spectrum: 132 $(M+H)^+$ $^{13}$C-NMR spectrum ($D_2O$, 125 MHz) ppm: 33.9, 44.5, 68.3, 71.6, 171.3

$^1$H-NMR spectrum ($D_2O$, 500 MHz) ppm: 2.18 (1H), 2.27 (1H), 3.52 (1H), 3.62 (1H), 4.18 (1H), 4.77 (1H)

The above-mentioned molecular weight data of the compound's mass spectrum and specific rotation, and the analytical results of its $^{13}$C-NMR spectrum and $^1$H-NMR spectrum were found to be identical to the data as described in the prior art [see J. Biol. Chem., 241, 1300 (1966), J. Antibiotics, 45, 824 (1992)] and to the data of cis-3- hydroxy-L-proline which was synthesized according to the methods of the prior art (see Liebigs Ann. Chem., 1881 (1979), Tetrahedron, 42, 2421 (1986)].

EXAMPLE 3

Production of Cis-3-hydroxy-L-proline

L-proline was hydroxylated by use of *Streptomyces canus* ATCC 12647, *Streptomyces canus* ATCC 12646, Bacillus sp. TH2 and Bacillus sp. TH3.

SR3 medium was put in test tubes (diameter 25 mm×length 200 mm) in an amount of 10 ml each and sterilized at 120° C. for 20 minutes. one loopful of cells of each of the microorganisms mentioned above that had grown in HT-agar plate medium was inoculated in the medium in a test tube and cultivated at 28° C. for 2 days by shaking. The resulting culture was used as a seed culture in the following steps.

Separately, Df4 medium comprising 2.5% glycerol, 2.5% glucose, 1.5% soybean meal, 0.05% dipotassium hydrogen phosphate, 0.05% magnesium sulfate 7 hydrate and 0. 5% calcium carbonate, and adjusted to pH 7.0 with 6N NaOH, was put in test tubes (diameter 25 mm×length 200 mm) in an amount of 10 ml each and sterilized at 120° C. for 20 minutes. One ml of each of the seed culture obtained above was inoculated in the medium in each test tube under germ-free conditions and cultivated at 28° C. for 1 day by shaking. The thus-obtained cultures were subjected to centrifugation at 15,000×g for 10 minutes at 4° C. The cells thus separated were washed with 80 mM TES buffer (pH 7.5) and then recentrifuged respectively.

The thus-obtained wet cells were suspended in 1 ml of the reaction mixture (a) as described in (1) of Example 1 respectively and allowed to stand at 30° C. for 3 hours.

As a result, it was verified that 242 $\mu$M, 202 $\mu$M, 318 $\mu$M and 141 $\mu$M of cis-3-hydroxy-L-proline were produced in the reaction mixture by use of the strains ATCC12647, ATCC12646, TH2 and TH3 respectively.

EXAMPLE 4

Production of Cis-3-hydroxy-L-proline

In the same manner as in Example 3 except that Df2 medium comprising 5% soluble starch, 1.5% dry yeast, 0.05% potassium dihydrogen phosphate, 0.05% magnesium sulfate 7 hydrate and 0.5% calcium carbonate and adjusted to pH 7.0 with 6N NaOH, and further containing 0.1% L-proline was used in place of Df4 medium. Each of Bacillus sp. TH2 and TH3 were cultivated.

As a result, it was verified that 745 $\mu$M (97.6 mg/l) of cis-3-hydroxy-L-proline for the strain TH2 and 327 $\mu$M (42.8 mg/l) for strain TH3 were produced in the aqueous medium.

EXAMPLE 5

Isolation and Purification of L-proline-3-hydroxylase (1) Preparation of Cell-free Extract Thirty grams of the wet cells obtained in (1) of Example 1 was suspended in 200 ml of Buffer (A) [20 mM piperazine buffer, pH was adjusted to 5.3 with 6N HCl, containing 1 mM dithiothreitol (DTT), 0.2 mM EDTA, 0.1% (v/v) Tween 20 and 10% (v/v) glycerol] while cooling with ice. The cells in the resulting suspension was disrupted by means of an ultrasonic cell disruptor while cooling with ice. The thus-disrupted cell suspension was subjected to centrifugation at 30,000×g at 4° C. for 30 minutes to separate a supernatant.

The subsequent operations were conducted under cooling with ice at a temperature of 4° C. or lower.

(2) Isolation and Purification by Column Chromatography (2)-1 Acid Treatment

The pH of the supernatant obtained in the previous step was adjusted at 4.5 with 6 N HCl, and the precipitate formed was removed therefrom through centrifugation as conducted at 15,000×g for 30 minutes to obtain a supernatant.

(2)-2 Resource Q Column Chromatography (I)

The supernatant obtained in the previous step was passed through a RESOURCE™ Q column (6 ml; produced by Pharmacia Co.) that had been equilibrated with Buffer (A). The column was washed with Buffer (A), and the fraction containing the desired enzyme was eluted with Buffer (A) having a linear concentration gradient of NaCl of 0 to 0.3M.

(2)-3 Resource Q Column Chromatography (II)

The active fraction obtained in the previous step was diluted 3-fold with Buffer (B) [20 mM TES buffer (pH7.5) containing 1 mM DTT, 0.2 mM EDTA and 10% (v/v) of glycerol] and was passed through a RESOURCE™ Q column (1 ml; produced by Pharmacia Co.) that had been equilibrated with Buffer (B). After the column was washed with Buffer (B), the fraction containing the enzyme was eluted with Buffer (B) having a linear concentration gradient of NaCl of 0 to 0.3 M.

(2)-4 Phenyl Sepharose Column Chromatography

NaCl was added to the active fraction obtained in the previous step until an NaCl concentration was 2M. The mixture was applied to a Phenyl Sepharose column (1 ml; Phenyl Sepharose HP HiLoad) that had been equilibrated with Buffer (B) containing 2M NaCl. The column was washed with Buffer (B) containing 2M NaCl, and the fraction containing the desired enzyme was eluted with Buffer (B) containing 0.1% (v/v) of Tween 20.

(2)-5 Resource Q Column Chromatograph (III)

The active fraction obtained in the previous step was de-salted using a PD-10 column (1 ml; produced by Pharmacia Co.), and the resulting mixture was passed through a RESOURCE™ Q column (1 ml) that had been equilibrated with Buffer (A). After the column was washed with Buffer (A), the fraction containing the desired enzyme was eluted with Buffer (A) having a linear concentration gradient of NaCl of 0 to 0.3 M.

(2)-6 Resource Q Column Chromatography (IV)

The active fraction obtained in the previous step was diluted 3-fold with Buffer (B) containing 0.1% (v/v) Tween 20 and passed through a RESOURCE™ Q column (1 ml; produced by Pharmacia Co.) that had been equilibrated with Buffer (B). The fraction containing the desired enzyme was eluted with Buffer B having a linear concentration gradient of NaCl of 0 to 0.3M.

The foregoing steps for the isolation and purification of the L-proline-3-hydroxylase are summarized in Table 9.

TABLE 9

Summary of Isolation and Purification of L-proline-3-Hydroxylase

| Fraction | Total Protein (mg) | Total Activity (U) | Relative Activity (U/mg protein) | Yield (%) |
|---|---|---|---|---|
| Cell-free Extract | 542 | 3540 | 6.5 | 100 |

TABLE 9-continued

Summary of Isolation and Purification of L-proline-3-Hydroxylase

| Fraction | Total Protein (mg) | Total Activity (U) | Relative Activity (U/mg protein) | Yield (%) |
|---|---|---|---|---|
| pH 4.5 Resource Q(I), pH 5.3 | 7.5 | 1553 | 207 | 44 |
| Resource Q(II), pH 7.5 | 3.3 | 1036 | 306 | 29 |
| Phenyl-Sepharose | 0.43 | 188 | 437 | 5.3 |
| Resource Q(III), pH 5.3 | 0.16 | 90.5 | 566 | 2.6 |
| Resource Q(IV), pH 7.5 | 0.035 | 60.3 | 1723 | 1.7 |

EXAMPLE 6

Properties of L-proline-3-Hydroxylase (1) Analysis by Electrophoresis

The purified enzyme preparation obtained in Example 5 was analyzed by sodium dodecylsulfate-polyacrylamide gel electrophoresis, using polyacrylamide gel PAGEL NPU-12.5L produced by Atto Co. and SDS-PAGE Molecular Weight Standard, Broad Range produced by Biorad Co. As a result, it was verified that the enzyme was composed of almost homogeneous sub-units having a molecular weight of approximately 35,000±5,000 daltons.

(2) Properties of the Enzyme

Using the reaction mixture mentioned below, the enzyme was subjected to the substrate omission and addition tests, by which the compounds indispensable to the enzyme reaction for hydroxylating L-proline at the 3-position of L-proline, the promoters for the enzyme reaction and the inhibitors against the enzyme reaction were investigated.

The reaction mixture was composed of 100 mM TES buffer (pH 7.0), 5 mM L-proline, 5 mM 2-ketoglutaric acid, 1 mM ferrous sulfate, 5 mM L-ascorbic acid and a predetermined amount of the pure enzyme, the total volume being 100 μl. The reaction was initiated by addition of the enzyme and continued for 10 minutes at 35° C. The reaction was stopped by heating the reaction mixture at 100° C. for 2 minutes. The amount of cis-3-hydroxy-L-proline formed in the reaction mixture was determined by the pre-column derivatization method using HPLC. One hundred microliters of 0.3 M boric acid buffer (pH 10.7), 4 μl of an aqueous solution of 10% (v/v) mercaptoethanol and 16 μl of ethanol solution of 5% (w/v) OPA were added to 100 μl of the reaction mixture, and the mixture was allowed to stand at 60° C. for 30 seconds. In addition, 50 μl of ethanol solution of 2% (w/v) NBD was added thereto and the mixture was allowed to stand at 60° C. for 40 minutes. The reaction was stopped by adding 30 μl of 1 N HCl to the reaction mixture, and the precipitates formed were removed therefrom by centrifugation and filtration. The cis-3-hydroxy-L-proline formed by the reaction was quantitatively determined by HPLC analysis.

The HPLC was carried out for the determination under the following conditions:

Mobile Phase: 10 mM Citric Acid (pH 4.0)/Methanol=3/1 (v/v)

Flow Rate: 1 ml/min

Column: YMC Pack ODS AQ-312 (produced by YMC Co., 6×150 mm)

Column Temperature: 50° C.

Detection: Fluorophotometry (excitation wavelength: 503 nm, emission wavelength: 541 nm)

The test results verified that L-proline, 2-ketoglutaric acid and $Fe^{++}$ ion are indispensable for the enzyme reaction for hydroxylating L-proline at the 3-position of L-proline, that L-ascorbic acid promotes the enzyme reaction and that $Zn^{++}$, $Cu^{++}$, $Co^{++}$, $Ba^{++}$ and EDTA inhibit the reaction.

The test results are shown in Table 10.

TABLE 10

Investigation of Components Influencing Enzyme Reaction of L-Proline-3-Hydroxylase

| Components in Reaction Mixture | Added (+)[2] Not Added(−) | Relative Activity[3] |
|---|---|---|
| Basic Reaction Mixture[1] | | 100 |
| | − Pure Enzyme | 0 |
| | − L-Proline | 0 |
| | − 2-Ketoglutaric Acid | 0 |
| | − $Fe^{++}$ | 0 |
| | − L-Ascorbic Acid | 25 |
| | + 2 mM EDTA | 5 |
| | + 1 mm $Zn^{++}$ | 0 |
| | + 1 mm $Cu^{++}$ | 4 |
| | + 1 mm $Co^{++}$ | 13 |
| | + 1 mm $Ba^{++}$ | 42 |

(3) Optimum pH Range

In the above-mentioned method of determining the enzymatic activity of the L-proline-3-hydroxylase, the reaction was carried out while the buffer component in the reaction mixture was changed to MES buffer [2-(N-morpholino)ethanesulfonic acid] at pH of 5.5 to 6.5, it was changed to PIPES buffer [piperazine-N,N'-bis(2-ethanesulfonic acid)] at pH of 6.5 to 7.5, it was changed to TES buffer at pH of 7.0 to 8.0, and it was changed to TAPS buffer (N-tris(hydroxymethyl)methyl-3-aminopropanesulfonic acid] at pH of 8.0 to 9.0. As a result, the enzyme had an activity of more than 80% of the maximum activity thereof at pH ranging from pH 6.5 to 7.5. The detailed test results are shown in Table 11 below.

TABLE 11

Optimum pH Range for the Enzyme Reaction

| pH | (buffer) | Relative Activity[1] |
|---|---|---|
| 5.5 | (MES) | 15.0 |
| 6.0 | (MES) | 70.9 |
| 6.5 | (PIPES) | 83.3 |
| 7.0 | (PIPES) | 92.1 |
| 7.0 | (TES) | 100.0 |
| 7.5 | (PIPES) | 80.4 |
| 7.5 | (TES) | 85.0 |
| 8.0 | (TES) | 72.2 |
| 8.0 | (TAPS) | 76.3 |
| 8.5 | (TAPS) | 52.9 |
| 9.0 | (TAPS) | 44.5 |

[1]The activity is indicated as a relative activity to the maximum activity being defined as 100.

(4) Stable pH Range

The enzyme solution in Buffer (B) was diluted 3-fold with 100 mM of a buffer (MES buffer at pH of 5.5 to 6.5, PIPES buffer at pH of 6.1 to 7.5, TES buffer at pH of 7.0 to 8.0, TAPS buffer at pH of 8.0 to 9.0), kept at 4° C. for 23 hours, and then its activity was determined. The enzyme kept at pH ranging from 6.5 to 8.0 had an activity of 80% or more of the original activity of the enzyme before the test. Accordingly, the enzyme was kept stable at pH ranging from 6.5 to 8.0.

(5) Temperature Range

In the above-mentioned of determining the enzyme activity of the proline-3-hydroxylase, the reaction was carried out at a temperature ranging from 15 to 50° C. for 15 minutes. As a result, the enzyme had an activity of 80% or more of the maximum activity thereof at temperatures ranging from 35 to 40° C. The detailed tests results are shown in Table 12 below.

TABLE 12

Optimum Temperature Range for the Enzyme Reaction

| Reaction Temperature (°C.) | Relative Activity[1] |
|---|---|
| 15 | 19 |
| 20 | 29 |
| 25 | 53 |
| 30 | 74 |
| 35 | 100 |
| 40 | 89 |
| 45 | 64 |
| 50 | 28 |

[1]The Activity is indicated as a relative activity to the maximum activity of being defined as 100.

(6) Stable Temperature Range

The enzyme was kept in Buffer (B) at temperatures ranging from 0 to 60° C. for 30 minutes and thereafter the activity of the enzyme was determined. As a result, the enzyme was inactivated at 50° C. or higher for 30 minutes.

(7) Km Value

The Km value is 0.49 mM for L-proline and is 0.11 mM for 2ketoglutaric acid, when determined in a TES buffer (pH 7.0) containing 5 mM L-ascorbic acid, 1 mM ferrous sulfate and a pre-determined amount of this enzyme.

(8) Isoelectric Point

The enzyme was analyzed, using Phast system (produced by Pharmacia Co.), to determine the isoelectric point of the enzyme. As a result, the isoelectric point of the enzyme was 4.3.

(9) N-terminal Amino Acid Sequence

The enzyme was analyzed, using Protein Sequencer Model PPSQ-10 (produced by Shimadzu Seisakusho K.K.), to determine the N-terminal amino acid sequence of the enzyme. The result is as follows:

SEQ ID NO: 5
(N-terminal)
1 MetArgSerHisIleLeuGlyArgIleGlu
11 LeuAspGlnGluArgLeuGlyArgAspLeu
21 GluTyrLeuAlaThrValProThrVal

EXAMPLE 7

Production of Cis-3-hydroxy-L-proline

The enzyme reaction using purified L-proline-3-hydroxylase obtained in Example 5 was carried out. The reaction mixture was composed of 200 mM TES buffer (pH 7.0), 20 mM L-proline, 20 mM 2-ketoglutarate, 5 mM L-ascorbic acids 1 mM, ferrous sulfate, and 106 U of purified enzyme preparation, the total volume being 100 μl. The reaction was carried out at 35° C. for 30 minutes. As a result of the reaction, 18mM (2.4 g/1) of cis-3-hydroxy-L-proline was produced in the reaction mixture.

EXAMPLE 8

Preparation of partial DNA fragment of the gene encoding L-proline-3-hydroxylase protein derived from Streptomyces sp. TH1

(1) Isolation of Chromosomal DNA of Streptomyces sp. TH1

Chromosomal DNA of Streptomyces sp. TH1 was isolated in the usual manner as follows. SK#2medium (comprising 0.25% glucose, 1.0% soluble starch, 0.25% yeast extract, 0.25% peptone, 0.15% meat extract, 0.01% potassium dihydrogen phosphate and 0.03% magnesium sulfate, and adjusted to a pH 7.6with 6 N NaOH) containing 5% mannitol and 0.05% glycine, was put in test tubes in an amount of 10 ml each, and sterilized at 120° C. for 20 minutes. One loopful of cells of Streptomyces sp. TH1 which had grown in TH-agar plate medium was inoculated in the above-mentioned SK#2 medium, and cultivated at 28° C. for 3 days with shaking.

The culture was centrifuged, and the obtained cells were washed with 10 ml of a 10.3% sucrose solution, and suspended in 6 ml of TS comprising 10.3% sucrose, 50 mM tris-HCl (pH 8.0) and 25 mM EDTA. One milliliter of a lysozyme solution (50 mg/ml·TS) was added thereto, and the mixture was incubated at 37° C. for 60 minutes. Subsequently, 0.6 ml of a Proteinase K (produced by Sigma Co.) solution (2 mg/ml·TS) was added to the lysozyme-treated solution, and gently stirred. Further, 3.6 ml of a 3.3% (w/v) SDS solution was added thereto while gently mixing, and the mixture was incubated at 37° C. for 60 minutes. The mixture was heated at 50° C. for 30 minutes, and then cooled with water. An equal amount of TE [containing 10 mM tris-HCl (pH 8.0) and 1 mM EDTA] saturated phenol-chloroform (1/1, v/v) was added thereto, and the mixed solution was moderately shaked for 30 minutes. After the centrifugation, the upper layer was taken, and again subjected to extraction with the mixture of TE saturated phenol-chloroform. The extract was centrifuged, and an equal amount of chloroform was then added to the upper layer, and mixed. The mixture was recentrifuged. The upper layer was taken, and 20 μl of an RNase A aqueous solution (10 mg/ml) heat-treated at 100° C. for 10 minutes were added to the upper layer. The mixture was incubated at 37° C. for 45 minutes. To the RNase A-treated solution were added 1/10 volume of a 5 M NaCl aqueous solution and 1/4 volume of 50% PEG6000, and gently mixed. The mixture was allowed to stand overnight while being cooled with ice. After the mixed solution was centrifuged at 12,000 rpm for 10 minutes, the supernatant was discarded completely, and the precipitate was dissolved in 5 ml of TE. After 1/10 volume of a 3 M sodium acetate solution and 1/30 volume of a 66 mM magnesium chloride solution were added thereto and mixed, 2.2 volumes of cold ethanol were added, and gently mixed. After the mixed solution was centrifuged at 10,000 rpm for 10 minutes, the supernatant was discarded, and the precipitate was washed twice with 70% cold ethanol. The precipitate containing 250 μg of chromosomal DNA was dissolved in TE and used in the subsequent experiment as chromosomal DNA.

(2) Determination of Partial Amino Acid Sequence of treptomyces sp. TH1-derived L-proline-3-hydroxylase Protein The N-terminal amino acid sequence of the purified enzyme obtained in Example 5 was sequenced, using Protein Sequencer Model PPSQ-10 (produced by Shimadzu Seisakusho Co.), to determine the N-terminal amino acid sequence thereof as indicated by SEQ ID NO: 5.

Furthermore, the purifed enzyme obtained in Example 5 was treated with lysyl endopeptidase in 0.1 M Tris-HCl with 4 M urea (pH 9), at 37° C. for 6 hours, and the thus-obtained peptide fragments were collected through HPLC. Their amino acid sequences were also analyzed in the same manner as above to determine the partial amino acid sequences as indicated by SEQ ID NOs: 6 and 7.

(3) Preparation of Partial DNA of L-proline-3-hydroxylase Gene

A sense chain mix DNA primer as indicated by SEQ ID NO: 8, which corresponds to the sequence of from the 1st to 6th amino acids in the amino acid sequence as indicated by SEQ ID NO: 5, and an anti-sense chain mix DNA primer as indicated by SEQ ID NO: 9, which corresponds to the sequence of from the 24th to 28th amino acids in the amino acid sequence as indicated by SEQ ID NO: 5, were synthesized, using 380A DNA Synthesizer (produced by Applied Biosystems Co.).

Using the above-synthesized DNAs as primers and the Streptomyces sp. TH1 chromosome DNA as template, the PCR was conducted using DNA Thermal Cycler 480 (produced by Perkin Elmer Cetus Co.).

The reaction was conducted using 20 μl of a reaction mixture having the following formulation.

Formulation of the reaction mixture:

21 Ng/μl of Streptomyces sp. TH1 chromosome DNA,

10 μM of sense chain mix DNA primer,

10 μM of anti-sense chain mix DNA primer, 0.125 U/μl of Pfu DNA polymerase (produced by STRATAGENE Co.), 10% of DMSO, 20 mM of Tris-HCl (pH 8.2), 10 mM of KCl, 6 mM of ammonium sulfate, 2 mM of magnesium chloride, 0.1% of Triton X-100, and 10 ng/μl of bovine serum albumin.

After the completion of an incubation at 95° C. for 5 minutes, a three step incubation, namely at 95° C. for 0.5 minute, at 25° C. for 0.5 minute and at 75° C. for 1 minute was repeated for a total of 40 times. The reaction mixture was subjected to electrophoresis with 15% polyacrylamide gel (PAGEL NPU-15L produced by Atto Co.), and the amplified 83 bp DNA was recovered using da Vinci Kun (Pen Touch Recovery NB-7000 Model) manufactured by Nippon Eido K.K.

Using the recovered DNA fragment (83 bp) as a template, the sense strand mix DNA primer indicated in SEQ ID NO: 8 as a primer and the anti-sense strand mix DNA primer indicated in SEQ ID NO: 10 corresponding to amino acids Nos. 21st to 25th of an amino acid sequence indicated in SEQ ID NO: 5 as a primer, the PCR was conducted again in the same manner, and the amplified 74 bp DNA was recovered. The thus-recovered DNA fragment was inserted into a Sma I site of pUC18 using Sure Clone Ligation Kit (produced by Pharmacia Co.), and the nucleotide sequence was determined by a nucleotide sequencing kit (Taq DyeDeoxy™ Terminator Cycle Sequencing Kit produced by Applied Biosystems).

The nucleotide sequences thus determined are indicated by SEQ ID NOs: 11 and 12. Thus, the two nucleotide sequences were determined. The amino acid sequence to be presumed from the nucleotide sequence of SEQ ID NO: 11 completely corresponded to the N-terminal amino acid sequence of the pure enzyme as indicated by SEQ ID NO: 1, except for the 2nd amino acid that could not be identified in the sequencing of the N-terminal amino acid sequence. The amino acid sequence to be presumed from the nucleotide sequence of SEQ ID NO: 12 exhibited high homology to the N-terminal amino acid sequence of the pure enzyme as indicated by SEQ ID NO: 5.

EXAMPLE 9

Cloning of a DNA fragment containing L-proline-3-hydroxylase Gene (1) Preparation of a Digoxigeniated (DIGated) Probe The two 74 bp fragments obtained in (3) of Example 8 and indicated by SEQ ID NOs: 11 and 12 each were inserted into the Sma I site of pUC18. Using each of these two plasmids thus obtained as a template, each plasmid was subjected to PCR in the same manner as in (3) of Example 8, using 50 μl of a reaction mixture containing 10 μM of the sense chain synthetic DNA as indicated by SEQ ID NO: 8 and 10 μM of the anti-sense chain synthetic DNA as indicated by SEQ ID NO: 10. The resulting reaction mixture each were subjected to 12.5% polyacrylamide gel electrophoresis to identify the formation of an amplified 74 bp fragment. From each gel, the amplified fragment was recovered in the same manner as in (3) of Example 8.

The 74 bp fragment was digoxigeniated (DIGated), using PCR DIG Labeling Kit (produced by Boehringer Mannheim Co.).

Using each of the thus-recovered two 74 bp fragments as a template, each fragment was subjected to PCR, using 2.5 U of Pfu DNA polymerase (produced by STRATAGENE Co.), 5 μl of 510 buffer for Pfu DNA polymerase (produced by STRATAGENE Co.), 5 μl of DMSO, 5 μl of 510 PCR DIG mix (produced by Boehringer Mannheim Co.) and 50 μl of a reaction mixture comprising 10 μM of the sense chain synthetic DNA of SEQ ID NO: 8 and 10 μM of the anti-sense chain synthetic DNA of SEQ ID NO: 10.

After the incubation at 95° C. for 5 minutes, the step of the incubation at 95° C. for 0.5 minute, at 50° C. for 0.5 minute and at 75° C. for 1 minute was repeated 40 times. After the reaction, each reaction mixture was subjected to 12.5% polyacrylamide gel electrophoresis to identify the formation of an amplified 74 bp fragment. From each gel, was recovered the amplified fragment in the same manner as in (3) of Example 8. The resulting two amplified fragments were used as probes. The probe derived from the nucleotide sequence of SEQ ID NO: 11 is referred to as probe A, and that from the nucleotide sequence of SEQ ID NO: 12 as probe B.

(2) Southern Hybridization

Twenty units of a restriction enzyme Pst I (produced by Takara Shuzo Co., LTD) was added to 20 μg of Streptomyces sp. TH1 chromosome DNA and reacted at 37° C. for 2 hours to cleave the DNA, which was then subjected to agarose gel electrophoresis. Using the probe A as obtained in (1) of Example 9, Southern hybridization was conducted with DIG Luminescent Detection Kit (produced by Boehringer Mannheim Co.) according to the method as described in the description attached to the kit.

Precisely, after the completion of the agarose gel electrophoresis, the gel was gently shaken in 0.25 N HCl for 20 minutes and then blotted onto Hybond-N⁺ membrane (produced by Amersham Co.) in 0.4M sodium hydroxide solution, while being sucked at 7.5 mmHg using Genopirator Pump AE-6680P (produced by ATTO Co.) and Genopirator AE-6680C (produced by ATTO Co.). The thus-blotted membrane was dried in air. The resulting membrane was dipped in 10 ml of a hybridization buffer of DIG Luminescent Detection Kit [comprising 50% v/v of formamide, 2% of a blocking reagent, 0.1% w/v of N-laurylsarcosine and 0.02% w/v of SDS in ×5 SSC (×1 SSC is comprised of 150 mM sodium chloride and 15 mM sodium citrate)] at 42° C. for 1 hour and thereafter dipped in a probe solution [prepared by adding 3 μl of the probe A as obtained in (1) of Example 9 to 200 μl of the hybridization buffer, then heating the mixture at 95° C. for 2 hours and thereafter adding thereto the hybridization buffer until the total volume was 1.5 ml], at 42° C. overnight. The thus-obtained membrane was washed twice each with 25 ml of ×2 SSC containing 0.1% of SDS for 5 minutes at room temperature and then twice each with 25 ml of ×0.1 SSC containing 0.1% of SDS for 15 minutes at 68° C.

After this, the membrane was treated with a washing buffer [buffer 1 (0.1 M maleic acid, 0.15 M sodium chloride, pH 7.5) containing 0.3% w/v of Tween-20] for 1 to 5 minutes at room temperature, then with 50 ml of buffer 2 (buffer 1 containing 1% of a blocking reagent) for 30 minutes at room temperature, then with 10 ml of buffer 2 containing 1 μl of anti-digoxigenin-AP Fab for 30 minutes at room temperature, then twice each with 50 ml of buffer 2 for 30 minutes at room temperature, then with 10 ml of buffer 3 (0.1 M Tris-HCl, 0.1 M sodium chloride, 50 mM magnesium chloride, pH 9.5) for from 2 to 5 minutes at room temperature, and then with 5 ml of buffer 3 containing 50 μl of Lumigen PPD for 5 minutes at room temperature, in that order. Subsequently, water was removed from the film quickly over a filter paper, then the film was wrapped with a wrapping film, Saran Wrap (poly vinylidene chloride film) and thereafter allowed to stand at 37° C. for 15 minutes. Using Hyperfilm ECL (produced by Amersham Co.), the resulting film was exposed at room temperature for 30 minutes.

A DNA fragment strongly hybridized with the probe and was detected at the position of approximately 6 kb.

The same process as in (2) of Example 9 was repeated, using the probe B as obtained in (1) of Example 9 and using 20 U of a restriction enzyme KpnI (produced by Takara Shuzo Co., LTD) in place of the restriction enzyme PstI. As a result, a DNA fragment strongly hybridized with the probe and was detected at the position of approximately 5 kb.

(3) Fractionation of Chromosome DNA

Twenty units of a restriction enzyme PstI (produced by Takara Shuzo Co., LTD) was added to 20 pg of Streptomyces sp. TH1 chromosome DNA and the mixture was allowed to stand at 37° C. for 2 hours to cleave the DNA, which was then mixed with the same amount, as that of the reaction mixture, of TE-saturated phenol/chloroform. The resulting mixture was centrifuged, and the upper layer was taken out. To the layer was added 2.2 times volume of cold ethanol and then gently mixed. This mixture was centrifuged at 10,000 rpm for 10 minutes, the supernatant was removed, and the precipitate was washed twice with 70% cold ethanol to obtain an ethanol precipitate. The process of obtaining the ethanol precipitate by using TE-saturated phenol/chloroform and cold ethanol is hereinafter referred to as an ethanol precipitation. The ethanol precipitate was dissolved in 120 μl of TE and subjected to agarose gel electrophoresis. After the completion of the electrophoresis, a DNA fraction at approximately 6 kb was extracted from the agarose gel and purified by the use of Prep-A-Gene (produced by Biorad Co.). Thus approximately 0.5 μg of a PstI-cleaved chromosome DNA fraction was obtained.

The same process as in (3) of Example 9 was repeated, except using 20 U of a restriction enzyme KpnI in place of PstI. Thus was obtained approximately 0.5 μg of a KpnI-cleaved chromosome DNA fraction at approximately 5 kb.

(4) Formation of Plasmid Library

1) After 1 μg of pBluescriptII KS(+) (produced by STRATAGENE Co.) was cleaved with restriction enzyme PstI (produced by Takara Shuzo Co., LTD) and then dephosphorylated with an alkaline phosphatase (derived from calf intestines) (produced by Takara Shuzo Co.,LTD) in accordance with the method described in the description attached to the product. After the completion of the reaction, the reaction mixture was subjected to ethanol precipitation to obtain an ethanol precipitate. The precipitate was dissolved in 5 μl of TE. The thus-obtained, PstI-cleaved pBluescriptII KS(+) DNA was reacted with 0.1 μg of PstI-cleaved chromosome DNA as obtained in (3) of Example 9, using a ligation kit (TAKARA Ligation Kit, produced by Takara Shuzo Co., LTD), for 2.5 hours at 26° C., whereby the two DNAs were ligated to each other. Using the thus-ligated DNA, E. coli XL2-Blue was transformed in a usual manner. The resulting transformant were spread on LB-agar medium containing 50 μg/ml of ampicillin and cultivated thereon overnight at 37° C. to obtain about 240 colonies.

2) After 1 μg of pBluescriptII KS(+) (produced by STRATAGENE Co.) was cleaved with a restriction enzyme KpnI (produced by Takara Shuzo Co., LTD), dephosphorylation was conducted with an alkaline phosphatase (derived from calf intestines) (produced by Takara Shuzo Co., LTD) in accordance with the method described in the description attached to the product. After the completion of the reaction, the reaction mixture was subjected to the ethanol precipitation to obtain an ethanol precipitate. The precipitate was dissolved in 5 μl of TE. The thus-obtained, KpnI-cleaved pBluescriptII KS(+) DNA was reacted with 0.1 μg of KpnI-cleaved chromosome DNA as obtained in (3) of Example 9, using a ligation kit (TAKARA Ligation Kit, produced by Takara Shuzo Co., LTD), for 2.5 hours at 26° C., whereby the two DNAs were ligated to each other. Using the thus-ligated DNA, E. coli XL2-Blue was transformed in a usual manner. The resulting transformant were spread on LB-agar medium containing 50 μg/ml of ampicillin and cultivated thereon overnight at 37° C. to obtain about 200 colonies.

(5) Selection of Intended Clone

The colonies having the desired clone was selected from the above-obtained colonies as follows.

Precisely, the colonies appearing on the LB-agar medium were transferred onto a nylon membrane (Nytran, produced by Schleicher & Schuell Co.) that has been previously washed with ×5 SSC, and the membrane was put on filter paper immersed with 0.5 M NaOH for 5 minutes. Subsequently, the film was put on filter paper immersed with 1.0 M Tris-HCl (pH 8.0) for 5 minutes and then on filter paper immersed with 1.5 M sodium chloride-1.0 M Tris-HCl (pH 8.0) for 5 minutes. After the film was lightly washed with ×2 SSC, then crosslinking was conducted by exposure to ultraviolet rays (120 mJ/cm$^2$). Then the surface of the film was wiped with ×2 SSC containing 0.1% of SDS, and the membrane was dried in air.

Using the DIGated probes as obtained in (1) of Example 9, positive colonies were detected on the membrane in accordance with the process as described in (2) of Example 9 using DIG Luminescent Detection Kit (produced by Boehringer Mannheim Co.).

Precisely, by the colony hybridization between about 240 colonies as obtained in 1) of Example 9(4) and the probe A, as obtained in (1) of Example 9, one positive colony having the intended clone was detected. By the colony hybridization between about 200 colonies as obtained in 2) of Example 9(4) and the probe B, as obtained in (1) of Example 9, five positive colonies each having the intended clone were detected.

From these colonies, plasmids were extracted inausual manner. Thus were obtained pTH30, pTH71 and pTH75.

Figure 1:
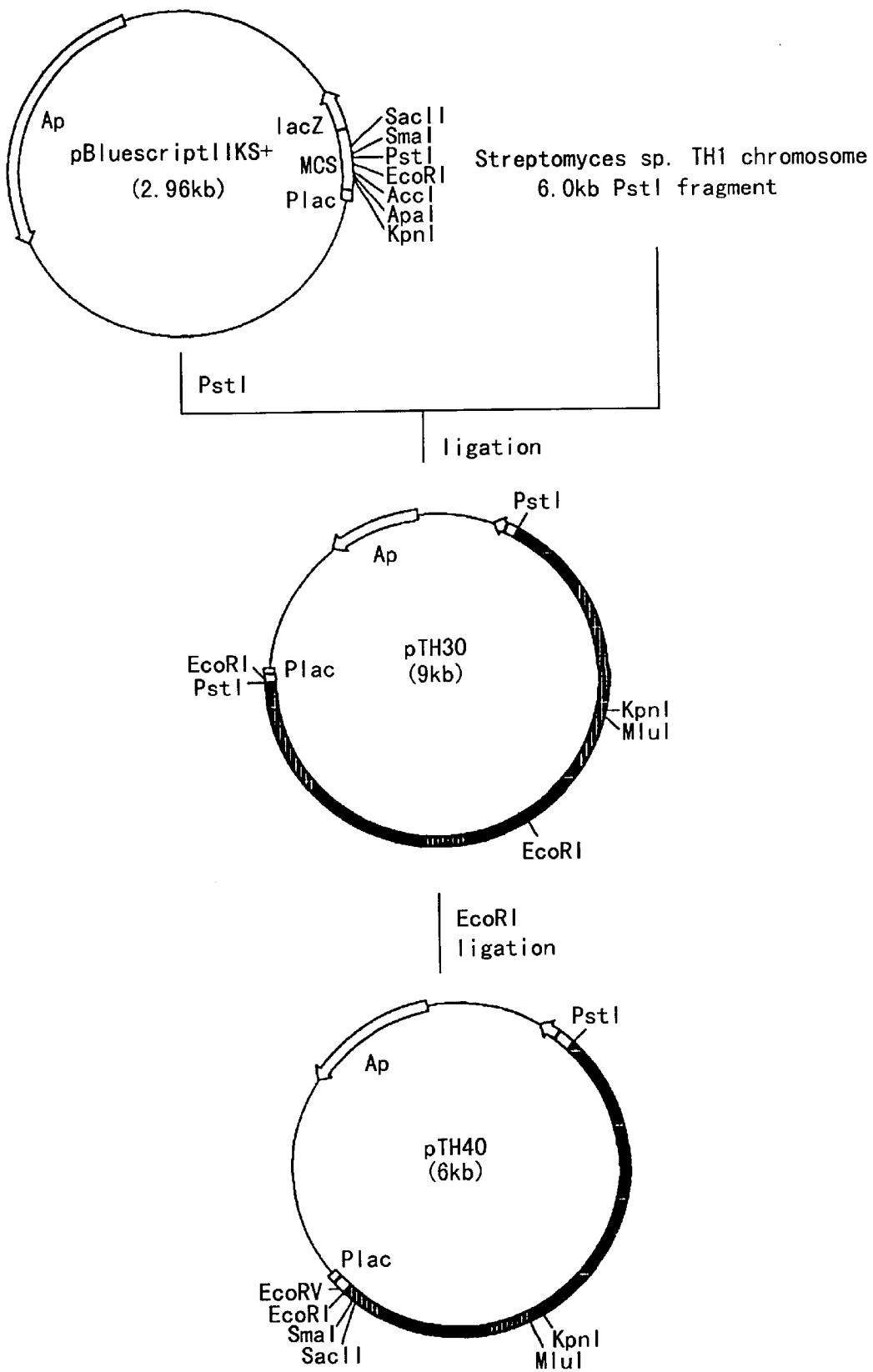
FIG. 1 shows the steps of constructing plasmid pTH30 and plasmid pTH40.

The structures of the plasmids were identified through digestion with restriction enzymes. The structure of pTH30 was such that a PstI-cleaved DNA fragment of approximately 6 kb was inserted into the PstI site of pBluescriptII KS(+) (see FIG. 1); while the structures of pTH71 and pTH75 were such that a KpnI-cleaved DNA fragment of approximately 5 kb was inserted into the KpnI site of pBluescriptII KS(+) in the opposite directions (see FIG. 2).

(6) Determination of Base Sequence

1) Using a deletion kit for kilosequences (produced by Takara Shuzo Co., LTD), plasmid pTH30 was processed to give various deletion mutant plasmids. The reagents and the process as indicated in the description attached to the kit were employed. The nucleotide sequences of the deletion plasmids were analyzed, using a base sequencing kit (Taq DyeDeoxy™ Terminator Cycle Sequencing Kit, produced by Applied Biosystems Co.), and the nucleotide sequence of 1081 b KpnI-EcoRI fragment as indicated by SEQ ID NO: 13 was identified.

In the nucleotide sequence thus identified, the nucleotide sequence indicated by SEQ ID NO: 3 that codes for the protein composed of 290 amino acid residues indicated by SEQ ID NO: 1 was present. The amino acid sequence comprises the N-terminal amino acid sequence indicated by SEQ ID NO: 5, which corresponded to the sequence of the pure L-proline-3-hydroxylase, and the internal amino acid sequences indicated by SEQ ID NO: 6 and 7, which revealed the existence of the intended L-proline-3-hydroxylase gene in the PstI fragment of approximately 6 kb obtained hereinabove. The gene is hereinafter referred to as L-proline-3-hydroxylase I-type gene.

2) The nucleotide sequence of the Streptomyces-derived insertion fragment terminal in each of plasmids pTH71 and pTH75 was analyzed, using a base sequencing kit (Taq DyeDeoxy™ Terminator Cycle Sequencing Kit, produced by Applied Biosystems Co.). On the basis of the thus-sequenced nucleotide sequence, a sequencing primer was synthesized using 380A Model DNA Synthesizer (produced by Applied Biosystems Co.). Using the primer, the nucleotide sequence of a part of each of pTH71 and pTH75 existing downstream from the Streptomyces-derived insertion fragment was analyzed. On the basis of the thus-sequenced nucleotide sequence, another sequencing primer was synthesized. Using the primer, apart of each of the plasmids existing further downstream was analyzed. The base sequencing operation comprising the above-mentioned steps was repeated, by which the NruI-KpnI fragment of 1826 bp was sequenced as in SEQ ID NO: 14.

The nucleotide sequence of the fragment thus sequenced comprised the nucleotide sequence indicated by SEQ ID NO: 4 that codes for the protein composed of 290 amino acid residues as indicated by SEQ ID NO: 2. The nucleotide sequence of SEQ ID NO: 4 comprised the nucleotide sequence indicated by SEQ ID NO: 12. The nucleotide sequence indicated by SEQ ID NO: 4 was homologous at 78.5% to the L-proline-3-hydroxylase I-type gene. The gene indicated by SEQ ID NO: 4 is hereinafter referred to as L-proline-3-hydroxylase II-type gene.

EXAMPLE 10

Construction of L-proline-3-hydroxylase Expression Plasmid (1) Construction of L-proline-3-hydroxylase I-type Gene Expression Plasmid Plasmid pTH30 as obtained in Example 9 was cleaved with a restriction enzyme EcoRI, and then self-ligated using a ligation kit (produced by Takara Shuzo Co., LTD). *E. coli* XL1-Blue MRF' strain was transformed with the DNA resulting from the self-ligation in a usual manner. A plasmid was extracted from the transformant in a usual manner, and the structure of the plasmid was identified through digestion with restriction enzyme.

As a result of the above, obtained was plasmid pTH40, from which had been removed the EcoRI fragment of approximately 3 kb existing in the 3'-side of L-proline-3-hydroxylase gene (see FIG. 4).

Subsequently, plasmid pTH40 was cleaved with KDnI and SmaI, then a fragment of approximately 0.95 kbp containing L-proline-3-hydroxylase I-type gene was identified through agarose gel electrophoresis, and the fragment was recovered from the agarose gel in a usual manner. The KpnI-SmaI-cleaved fragment was inserted into the KpnI-SmaI-cleaved site of pBluescriptII KS(+), using a ligation kit (produced by Takara Shuzo Co., LTD). With the resulting DNA, *E. coli* XL1-Blue MRF' strain was transformed in a usual manner. The resulting transformant was spread on LB-agar medium containing 50 μg/ml of ampicillin and cultivated thereon overnight at 37° C. A plasmid was extracted from the colonies of the transformant thus grown in a usual manner, and its structure was identified through digestion with restriction enzyme.

As a result of the above, a plasmid pTH50, into which had been inserted the DNA fragment coding for L-proline-3-hydroxylase I-type gene in the same direction as that for transcription of lac promoter (see FIG. 3) was obtained.

(2) Construction of L-proline-3-hydroxylase II-type Gene Expression Plasmid

Plasmid pTH75 as obtained in Example 9 was cleaved with restriction enzymes NruI and SacI, and thus-cleaved fragment of approximately 1900 bp containing L-proline-3-hydroxylase II-type gene was recovered through agarose gel electrophoresis. The NruI-SacI-cleaved fragment was inserted into the HincII-SacI-cleaved site of pBluescriptII KS (+), using a ligation kit (produced by Takara Shuzo Co., LTD). With the resulting DNA, *E. coli* XL2-Blue MRF' strain was transformed in a usual manner. The resulting transformant was spread on LB-agar medium containing 50 μg/ml of ampicillin and cultivated thereon overnight at 37° C. A plasmid was extracted from the colonies of the transformant thus grown in a usual manner, and its structure was identified through digestion with restriction enzyme.

As a result of the above, a plasmid pEX1-5, into which had been inserted the DNA fragment coding for L-proline-3-hydroxylase II-type gene in the direction same as that for transcription of lac promoter (see FIG. 4) was obtained.

EXAMPLE 11

Production of L-proline-3-hydroxylase by Transformants (1) Production of L-proline-3-hydroxylase by Transformant Having L-proline-3-hydroxylase I-type Gene

*E. coli* ATCC12435 was transformed with plasmid pTH50 as obtained in Example 10. The resulting transformant was inoculated in 3 ml of an LB medium containing 50 μg/ml of ampicillin and cultivated therein overnight at 30° C. by shaking. The resulting culture was centrifuged. If desired, the thus-obtained wet cells were frozen and stored at −20° C., and the fozen cells were thawed before use.

Added to 250 μl of a reaction mixture [containing 12 mM L-proline, 24 mM 2-ketoglutaric acid, 4 mM ferrous sulfate and 8 mM L-ascorbic acid in 200 mM TES buffer (pH 7.5)] at 4% (w/v) in terms of the wet cells, and the mixture was allowed to stand for 10 minutes at 35° C. The reaction mixture was heated at 100° C. for 2 minutes to stop the reaction.

The resulting reaction mixture was centrifuged, and 100 μl of 0.3 M borate buffer (pH 10.7), 4 μl of 10% (v/v) mercaptoethanol aqueous solution and 16 μl of 5% (w/v) OPA in ethanol were added to 100 μl of the resulting supernatant and left at 60° C. for 30 seconds, and then 50 μl of 2% (w/v) NBD in ethanol was added thereto. The mixture was allowed to stand at 60° C. for 40 minutes. Then 30 μl of 1 N hydrochloric acid was added to the reaction mixture to stop the reaction. The resulting reaction mixture was centrifuged and filtered through a filter to remove the precipitate therefrom, and the resulting filtrate was analyzed through HPLC by which the product cis-3-hydroxy-L-proline produced was quantitatively determined.

HPLC was conducted under the following conditions.

Mobile Phase: 10mM citric acid (pH 4.0)/methanol=3/1 (v/v).

Flow Rate: 1 ml/min.

Column: YMC Pack ODS AQ-312 (produced by YMC Co., 6×150 mm).

Column Temperature: 50° C.

Detection: fluorophotometry excitation wavelength: 503 nm emission wavelength: 541 nm.

As is shown in Table 13 below, the transformant E. coli ATCC12435/pTH50 produced L-proline-3-hydroxylase more by approximately 34 times/cell than the Streptomyces sp. TH1 strain which had been used as the gene source.

TABLE 13

L-proline-3-hydroxylase Activity Produced by Transformant

| Strain | Cell Activity[1] | Relative Activity[2] |
| --- | --- | --- |
| E. coli ATCC12435/pTH50 | 1.94 | 34.0 |
| E. coli ATCC12435/pBluescriptII KS (+) | Not detected. | — |
| Streptomyces sp. TH1[3] | 0.057 | 1 |

[1]Cell activity indicates the enzymatic activity per mg of wet cells (U/mg wet cells). One U indicates the enzymatic activity of producing 1 nmol of cis-3-hydroxy-L-proline per minute (nmol/min).
[2]Relative activity is based on the enzymatic activity produced by Streptomyces sp. TH1 strain of being 1 (one).
[3]This is referred to in (2) of Example 1.

(2) Production of L-proline-3-hydroxylase by Transformant Having L-proline-3-hydroxylase II-type Gene E. coli ATCC12435 was transformed with plasmid pEX1-5 as obtained in Example 10. The resulting transformant was inoculated in 3 ml of a TB medium containing 50 μg/ml of ampicillin and cultivated therein overnight at 30° C. by shaking. The resulting culture was centrifuged, and the cells were collected. If desired, the cells were frozen and stored at −20° C., and the frozen cells were thawed before use.

The cells were added to 500 μl of a reaction mixture [containing 25 mM L-proline, 50 mM 2-ketoglutaric acid, 4 mM ferrous sulfate and 8 mM L-ascorbic acid in 200 mM TES buffer (pH 7.5)] at 2.2% (w/v) in terms of the wet cells, and reacted for 15 minutes at 35° C. The reaction mixture was heated at 100° C. for 2 minutes to stop the reaction.

The resulting reaction mixture was centrifuged, and 100 μl of 0.3 M borate buffer (pH 10.7), 4 μl of 10% (v/v) mercaptoethanol aqueous solution and 16 μl of 5% (w/v) OPA in ethanol were added to 100 μl of the resulting supernatant and left at 60° C. for 30 seconds, and thereafter the mixture was neutralized. This treatment resulted in modification of primary amino acids with OPA but not the secondary amino acid, hydroxyproline. The thus-processed reaction mixture was analyzed through HPLC, by which the product of cis-3-hydroxy-L-proline produced was quantitatively determined. HPLC was conducted under the following conditions.

Mobile Phase: aqueous solution of 1 mM copper sulfate.

Flow Rate: 1 ml/min.

Column: SUMICHIRAL OA-5000 (produced by Sumika Chemical Analysis Service Co., 4.6×250 mm)

Column Temperature: 38° C.

The eluate as optically resolved under the conditions mentioned above was on-line mixed with reactants mentioned below under the conditions mentioned below, in which the eluate was modified with NBD in a reaction box CRB-6A (produced by Shimadzu Co.) and the NBDated-secondary amino acid was quantitatively determined through fluorophotometry.

| Reactants and Amounts Thereof Added: | |
| --- | --- |
| aqueous solution of | 300 mM boric acid and 25 mM EDTA (pH 9.6) 0.2 ml/min. |
| 1 g/liter methanol of NBD: | 0.5 ml/min. |
| Reaction Temperature: | 60° C. |
| Detection: | fluorophotometry excitation wavelength 503 nm emission wavelength 541 nm |

As is shown in Table 14 below, the transformant E. coli ATCC12435/pEX1-5 produced L-proline-3-hydroxylase more by approximately 77 times/cell than the Streptomyces sp. TH1 strain which had been used as the gene source.

TABLE 14

L-proline-3-hydroxylase Activity Produced by Transformant

| Strain | Cell Activity[1] | Relative Activity[2] |
| --- | --- | --- |
| E. coli ATCC12435/pEX1-5 | 4.42 | 77.5 |
| E. coli ATCC12435/pBluescriptII KS (+) | Not detected. | — |
| Streptomyces sp. TH1[3] | 0.057 | 1 |

[1]Cell activity indicates the enzymatic activity per mg of wet cells (U/mg wet cells). One U indicates the enzymatic activity of producing 1 nmol of cis-3-hydroxy-L-proline per minute (nmol/min).
[2]Relative activity is based on the enzymatic activity produced by Streptomyces sp. TH1 strain of being 1 (one).
[3]This is referred to in (2) of Example 1.

EXAMPLE 12

Construction of Expression Plasmid for a Fused Protein with a β-galactosidase Protein Fragment (1) Construction of pTH60 Plasmid Four micrograms of pTH40 DNA was cleaved with MluI and subjected to ethanol precipitation to obtain an ethanol precipitate. The thus-obtained ethanol precipitate (DNA fragment) was dissolved in 36 μl of TE, and the both terminals of the DNA fragment were blunted using Takara DNA Blunting Kit (produced by Takara Shuzo Co., LTD). The resulting DNA fragment was recovered through ethanol precipitation. The DNA was cleaved with EcoRI and subjected to agarose gel electrophoresis, a fragment of approximately 1 kb containing the structural gene of L-proline-3-hydroxylase was extracted from the agarose gel and recovered in a usual manner using Pre-A-Gene (produced by Biorad Co.). The DNA fragment was then dissolved in 10 μl of TE.

On the other hand, 2.4 μg of plasmid pBluescriptII KS(+) DNA was cleaved with ApaI and subjected to agarose gel electrophoresis. The DNA fragment was then recovered from the gel and purified in a usual manner. Using Takara DNA Blunting Kit (produced by Takara Shuzo Co., LTD), the both terminals of the DNA fragment were blunted. The thus-blunted DNA fragment was cleaved with EcoRI and then subjected to ethanol precipitation to obtain an ethanol precipitate. The ethanol precipitate was dissolved in 5 μl of TE.

The above-obtained MluI-EcoRI fragment of approximately 1 kb containing the structural gene of L-proline-3- hydroxylase was ligated to the ApaI-EcoRI-cleaved pBluescriptII KS(+), using a ligation kit (produced by Takara Shuzo Co., LTD).

With the ligated DNA, *E. coli* XL1-Blue MRF' strain was transformed in a usual manner. The resulting transformant was spread on LB-agar medium containing 50 µg/ml of ampicillin and then cultivated thereon overnight at 37° C. A plasmid was extracted from the grown colonies of the transformant in a usual manner, and its structure was identified through digestion with restriction enzyme.

As a result of the above, a plasmid pTH60, into which had been inserted the structural gene of L-proline-3-hydroxylase as fused with the N-terminal amino acid sequence of β-Gal, in the direction same as that for transcription of lac promoter (see FIG. 5) was obtained. The structure of the amino acid sequence of the fused protein thus constructed hereinabove was such that the N-terminal sequence of β-Gal comprised of 21 amino acids has been fused to the L-proline-3-hydroxylase protein via arginine (22nd) as newly formed at the DNA bonding site. However, methionine (GTG) which is the first amino acid of the L-proline-3-hydroxylase protein is translated as valine. The amino acid sequence of the fused protein is indicated by SEQ ID NO: 15.

(2) pTH70 Plasmid pBluescriptII KS(+) DNA (2.4 µg) was cleaved with AccI and subjected to ethanol precipitation to obtain an ethanol precipitate (DNA fragment). The both terminals of the DNA fragment were blunted using Takara DNA Blunting Kit (produced by Takara Shuzo Co., LTD). The resulting DNA fragment was cleaved with EcoRI and then subjected to ethanol precipitation to obtain an ethanol precipitate. The ethanol precipitate was dissolved in 5 µl of TE.

The MluI-EcoRI fragment of approximately 1 kb containing the structural gene of L-proline-3-hydroxylase, which had been obtained in (1) of Example 12, was ligated to the AccI-EcoRI-cleaved pBluescriptII KS(+), using a ligation kit (produced by Takara Shuzo Co., LTD).

With the ligated DNA, *E. coli* XL1-Blue MRF' strain was transformed in a usual manner. The resulting transformant was spread on LB-agar medium containing 50 µg/ml of ampicillin and then cultivated thereon overnight at 37° C. A plasmid was extracted from the grown colonies of the transformant in a usual manner, and its structure was identified through digestion with restriction enzyme.

As a result of the above, a plasmid pTH70, into which had been inserted the structural gene of L-proline-3-hydroxylase as fused with the N-terminal amino acid sequence of β-Gal in the direction same as that for transcription of lac promoter (see FIG. 6) was obtained. The structure of the amino acid sequence of the fused protein thus constructed hereinabove was such that the N-terminal sequence of β-Gal comprised of 27 amino acids has been fused to the L-proline-3-hydroxylase via arginine (28th) as newly formed at the DNA bonding site. However, methionine (GTG) which is the first amino acid of the L-proline-3-hydroxylase protein is translated as valine. The amino acid sequence of the fused protein is indicated by SEQ ID NO: 16.

(3) pTH80 Plasmid

Four micrograms of pTH40 DNA was cleaved with MluI and subjected to ethanol precipitation to obtain an ethanol precipitate. The ethanol precipitate (DNA fragment) was dissolved in 36 µl of TE. The both terminals of the DNA fragment were blunted using Takara DNA Blunting Kit (produced by Takara Shuzo Co., LTD). The resulting DNA fragment cleaved with SacII and then subjected to agarose gel electrophoresis. After the electrophoresis, a fragment of approximately 0.95 kb containing the structural gene of L-proline-3-hydroxylase was extracted from the gel and recovered in a usual manner using Prep-A-Gene (produced by Biorad Co.). The thus-recovered fragment was then dissolved in 10 µl of TE.

On the other hand, 2.4 µg of plasmid pBluescriptII KS(+) DNA was cleaved with PstI and subjected to ethanol precipitation to obtain an ethanol precipitate (DNA fragment). This DNA fragment was dissolved in 36 µl of TE, and the both terminals of the DNA fragment were blunted using Takara DNA Blunting Kit (produced by Takara Shuzo Co., LTD). The resulting DNA fragment was then cleaved with SacII and subjected to ethanol precipitation to obtain an ethanol precipitate (DNA fragment). The DNA fragment was then dissolved in 5 µl of TE.

The MluI-SacII fragment of approximately 1 kb containing the structural gene of L-proline-3-hydroxylase, which had been obtained in the above, was ligated to the PstI-SacII-cleaved pBluescriptII KS(+), using a ligation kit (produced by Takara Shuzo Co., LTD).

With the ligated DNA, *E. coli* XL1-Blue MRF' strain was transformed in a usual manner. The resulting transformant was spread on LB-agar medium containing 50 µg/ml of ampicillin and then cultivated thereon overnight at 37° C. A plasmid was extracted from the grown colonies of the transformant in a usual manner, and its structure was identified through digestion with restriction enzyme.

As a result of the above, a plasmid pTH80, into which had been inserted the structural gene of L-proline-3-hydroxylase as fused with the N-terminal amino acid sequence of β-Gal in the direction same as that for transcription of lac promoter (see FIG. 7) was obtained. The structure of the amino acid sequence of the fused protein thus constructed hereinabove was such that the N-terminal sequence of β-Gal comprised of 37 amino acids has been fused to the L-proline-3-hydroxylase protein via arginine (38th) as newly formed at the DNA bonding site. However, methionine (GTG) which is the first amino acid of the L-proline-3-hydroxylase protein is translated as valine. The amino acid sequence of the fused protein is indicated by SEQ ID NO: 17.

EXAMPLE 13

Production of L-proline-3-hydroxylase by Transformant Having Fused Protein Expression Plasmid

*E. coli* ATCC12435 was transformed with any one of plasmids pTH60, pTH70 and pTH80 as obtained in Example 12. In the same manner as in Example 11, the resulting transformant was cultivated, and the productivity of L-proline-3-hydroxylase by the transformant cells was detected.

As shown in Table 15 below, the transformant produced L-proline-3-hydroxylase in an amount of 46 to 121 times per cell in comparison to Streptomyces sp. TH1 strain which had been used as the gene source.

TABLE 15

L-proline-3-hydroxylase Activity Produced by Transformants

| Strain | Cell Activity[1] | Relative Activity[2] |
|---|---|---|
| *E. coli* ATCC12435/pTH60 | 5.19 | 91.1 |
| *E. coli* ATCC12435/pTH70 | 6.90 | 121.1 |
| *E. coli* ATCC12435/pTH80 | 2.63 | 46.1 |
| *E. coli* ATCC12435/pBluescriptII | Not | — |

TABLE 15-continued

L-proline-3-hydroxylase Activity Produced by Transformants

| Strain | Cell Activity[1] | Relative Activity[2] |
|---|---|---|
| KS (+) | detected. | |
| Streptomyces sp. TH1[3] | 0.057 | 1.0 |

[1] Cell activity indicates the enzymatic activity per mg of wet cells (U/mg wet cells). One U indicates the enzymatic activity of producing 1 nmol of cis-3-hydroxy-L-proline per minute (nmol/min).
[2] Relative activity is based on the enzymatic activity produced by Streptomyces sp. TH1 strain of being 1 (one).
[3] This is referred to in (2) of Example 1.

EXAMPLE 14

Production of Cis-3-hydroxy-L-proline by Transformant (1) Production of Cis-3-hydroxy-L-proline by Transformant E. coli ATCC12435/pTH70

Cis-3-hydroxy-L-proline was produced using the transformant E. coli ATCC12435/pTH70 as obtained in Example 13.

Precisely, the transformant of E. coli ATCC12435/pTH70 was inoculated in 3 ml of a TB medium (comprising 12 g of bactotripton, 24 g of bactoyeast extract, 4 g of glycerol, 2.3 g of $KH_2PO_4$ and 12.5 g of dipotassium phosphate in one liter of distilled water and sterilized at 120° C. for 20 minutes) containing 100 μg/ml of ampicillin, and cultivated therein at 30° C. for 16 hours by shaking culture. The resulting culture was centrifuged, and the amount of cis-3-hydroxy-L-proline in the supernatant thus separated was quantitatively determined.

As a result, 620 μM (81.1 mg/liter) of cis-3-hydroxy-L-proline was formed in the supernatant of the culture of E. coli ATCC12435/pTH70.

On the other hand, free cis-3-hydroxy-L-proline was not detected in the supernatant of the culture of the E. coli ATCC12435 which had been used as the host.

(2) Production of Cis-3-hydroxy-L-proline by Transformant E. coli ATCC12435/pTH70

The transformant of E. coli ATCC12435/pTH70 obtained in Example 13 was inoculated in 50 ml of a Med4 medium containing 100 μg/ml of ampicillin, and cultivated therein at 30° C. for 16 hours by shaking.

The culture was used as a seed culture, which was inoculated in a 5-liter jar fermenter containing therein 2 liters of a Med6 medium. 200 mM of L-proline and 100 μg/ml of ampicillin were added thereto, and the transformant was cultivated in the fermenter under the condition of 400 rpm and 1 vvm, at 30° C.

During the cultivation, glucose and L-proline were suitably added to the medium in such a manner that glucose was always present in the medium and L-proline could be at about 50 mM therein, and the lowermost limit of the pH of the medium was controlled at 6.5 by adding $NH_4OH$ to the medium.

The culture was centrifuged, and the amount of cis-3-hydroxy-L-proline in the supernatant separated was quantitatively determined. Seventy two hours after the start of the incubation, 115 mM (15 g/liter) of cis-3-hydroxy-L-proline was produced and accumulated in the supernatant of the culture of E. coli ATCC12435/pTH70.

On the other hand, free cis-3-hydroxy-L-proline was not detected in the supernatant of the culture of E. coli ATCC12435 which had been used as the host.

EXAMPLE 15

Conversion of L-proline into Cis-3-hydroxy-L-proline with Transformant cells

Using the transformant E. coli ATCC12435/pTH70 as obtained in Example 13, L-proline was converted into cis-3-hydroxy-L-proline.

Precisely, the transformant was inoculated in 10 ml of an LB medium containing 50 μg/ml of ampicillin and cultivated therein overnight at 30° C. by shaking. Then 7 ml of the culture was centrifuged to collect the cells (wet cells). If desired, the cells were frozen and stored at -20° C. and thawed before use.

After 10% (w/v) of the wet cells were added to 500 μl of a reaction mixture [comprising 24 mM L-proline, 24 mM 2-ketoglutaric acid, 4 mM ferrous sulfate and 8 mM L-ascorbic acid in 200 mM TES buffer (pH 7.5)], reaction was conducted at 35° C. for 60 minutes. The amount of cis-3-hydroxy-L-proline as formed in the reaction mixture was quantitatively determined. As a result, 17.7 mM (2.3 g/liter) of cis-3-hydroxy-L-proline was formed in the reaction mixture.

What is claimed is:

1. An isolated gene coding for a protein having an N-terminal amino acid sequence of SEQ ID NO: 5, which has the enzymatic ability of hydroxylating the 3-position of L-proline end which acts on free L-proline in the presence of 2-ketoglutaric acid and divalent iron ions to produce cis-3-hydroxy-L-proline.

2. The gene according to claim 1, wherein the gene codes for a protein having the amino acid sequence selected from SEQ ID NOs : 1, 2, 15, 16 and 17.

3. The gene according to claim 1, wherein the gene is selected from the nucleotide sequences of SEQ ID NOs: 3, 4, 13 and 14.

4. The gene according to claim 1, wherein the gene is derived from microorganisms belonging to the genus Streptomyces or Bacillus.

5. The gene according to claim 4, wherein the microorganisms are selected from those of *Streptomyces canus* ATCC12647, *Streptomyces canus* ATCC12646, Streptomyces sp. TH1 (FERM BP-4399), Bacillus sp. TH2 (FERM BP-4397) and Bacillus sp. TH3 (FERM BP-4398).

6. A recombinant DNA constructed by inserting into a vector a DNA fragment that codes for a protein having an N-terminal amino acid sequence of SEQ ID NO: 5, which has the enzymatic ability of hydroxylating the 3-position of L-proline 5 and which acts on free L-proline in the presence of 2-ketoglutaric acid and divalent iron ions to produce cis-3-hydroxy-L-proline.

7. A recombinant DNA according to claim 6, wherein the gene codes for a protein having the amino acid sequence selected from the sequences of Sequence Nos. 1, 2, 15, 16 and 17.

8. The recombinant DNA according to claim 6, wherein the gene is selected from the nucleotide sequences of SEQ ID NOs: 3, 4, 13 and 14.

9. The recombinant DNA according to claim 6, wherein the gene is derived from microorganisms belonging to the genus Streptomyces or Bacillus.

10. The recombinant DNA according to claim 9, wherein the microorganisms are selected from those of *Streptomyces canus* ATCC12647, *Streptomyces canus* ATCC12646, Streptomyces sp. TH1 (FERM BP-4399), Bacillus sp. TH2 (FERM BP-4397) and Bacillus sp. TH3 (FERM BP-4398).

11. A transformant having a recombinant DNA constructed by inserting into a vector a DNA fragment that codes for a protein having the N-terminal amino acid sequence of SEQ ID NO: 5, which has the enzymatic ability of hydroxylating the 3-position of L-proline and which acts on free L-proline in the presence of 2-ketoglutaric acid and divalent iron ions to produce cis-3-hydroxy-L-proline.

12. The transformant according to claim 11, wherein the gene codes for a protein having the amino acid sequence selected from the sequences of Sequence Nos. 1, 2, 15, 16 and 17.

13. The transformant according to claim 11, wherein the gene is selected from nucleotide sequences of SEQ ID NOs: 3, 4, 13 and 14.

14. The transformant according to claim 11, wherein the gene is derived from microorganisms belonging to the genus Streptomyces or Bacillus.

15. The transformant according to claim 14, wherein the microorganisms are selected from those of *Streptomyces canus* ATCC12647, *Streptomyces canus* ATCC12646, Streptomyces sp. TH1 (FERM BP-4399), Bacillus sp. TH2 (FERM BP-4397) and Bacillus sp. TH3 (FERM BP-4398).

16. The transformant according to claim 11, which is selected from *Escherichia coli* XL2-Blue/pTH30 (FERM BP-5026) and from *Escherichia coli* XL2-Blue/pTH75 (FERM BP-5409).

17. A recombinant method for producing L-proline-3-hydroxylase, which comprises culturing in a medium a transformant, prepared by inserting into a vector a DNA fragment that codes for the hydroxylase having the N-terminal amino acid sequence of SEQ ID NO: 5, which has the enzymatic ability of hydroxylating the 3-position of L-proline and which acts on free L-proline in the presence of 2-ketoglutaric acid and divalent iron ions to produce cis-3-hydroxy-L-proline, thereby producing and accumulating L-proline-3-hydroxylase, followed by collecting the L-proline-3-hydroxylase from the resulting culture.

18. The method for producing L-proline-3-hydroxylase according to claim 17, wherein L-proline is added to the medium.

19. The method for producing L-proline-3-hydroxylase according to claim 17 or 18, wherein the gene codes for a protein having the amino acid sequence selected from SEQ ID NOs: 1, 2, 15, 16 and 17.

20. The method for producing an L-proline-3-hydroxylase according to claim 17 or 18, wherein the gene is selected from nucleotide sequences of SEQ ID NOs: 3, 4, 13 and 14.

21. The method for producing L-proline-3-hydroxylase according to claim 17 or 18, wherein the gene is derived from microorganisms belonging to the genus Streptomyces or Bacillus.

22. The method for producing L-proline-3-hydroxylase according to claim 21, wherein the microorganisms are selected from *Streptomyces canus* ATCC12647, *Streptomyces canus* ATCC12646, Streptomyces sp. TH1 (FERM BP-4399), Bacillus sp. TH2 (FERM BP-4397) and Bacillus sp. TH3 (FERM BP-4398).

23. An isolated gene encoding L-proline-3-hydroxylase from Streptomyces or Bacillus selected from SEQ ID NOs: 1, 2, 15, 16 and 17.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 290 amino acids
      (B) TYPE: amino acid
      (D) TOPOLOGY: linear (ii) MOLECULE TYPE: protein (vi) ORIGINAL SOURCE:
      (A) ORGANISM: Streptomyces sp.
      (B) STRAIN: TH1

(xi) SEQUENCE DESCRIPTION: SEQ ID NO:1:

Met Arg Ser His Ile Leu Gly Arg Ile Glu Leu Asp Gln Glu Arg Leu
1               5                   10                  15

Gly Arg Asp Leu Glu Tyr Leu Ala Thr Val Pro Thr Val Glu Glu Glu
            20                  25                  30

Tyr Asp Glu Phe Ser Asn Gly Phe Trp Lys Asn Ile Pro Leu Tyr Asn
        35                  40                  45

Ala Ser Gly Gly Ser Glu Asp Arg Leu Tyr Arg Asp Leu Glu Gly Ser
    50                  55                  60

Pro Ala Gln Pro Thr Lys His Ala Glu Gln Val Pro Tyr Leu Asn Glu
65                  70                  75                  80

Ile Ile Thr Thr Val Tyr Asn Gly Glu Arg Leu Gln Met Ala Arg Thr
                85                  90                  95

Arg Asn Leu Lys Asn Ala Val Val Ile Pro His Arg Asp Phe Val Glu
            100                 105                 110

Leu Asp Arg Glu Leu Asp Gln Tyr Phe Arg Thr His Leu Met Leu Glu
        115                 120                 125

Asp Ser Pro Leu Ala Phe His Ser Asp Asp Thr Val Ile His Met
    130                 135                 140

Arg Ala Gly Glu Ile Trp Phe Leu Asp Ala Ala Val His Ser Ala
145                 150                 155                 160

Val Asn Phe Ala Glu Phe Ser Arg Gln Ser Leu Cys Val Asp Leu Ala
            165                 170                 175

Phe Asp Gly Ala Phe Asp Glu Lys Glu Ala Phe Ala Asp Ala Thr Val
        180                 185                 190

Tyr Ala Pro Asn Leu Ser Pro Asp Val Arg Glu Arg Lys Pro Phe Thr
    195                 200                 205

Lys Glu Arg Glu Ala Gly Ile Leu Ala Leu Ser Gly Val Ile Gly Arg
210                 215                 220

Glu Asn Phe Arg Asp Ile Leu Phe Leu Leu Ser Lys Val His Tyr Thr
225                 230                 235                 240

Tyr Asp Val His Pro Gly Glu Thr Phe Glu Trp Leu Val Ser Val Ser
            245                 250                 255

Lys Gly Ala Gly Asp Asp Lys Met Val Glu Lys Ala Glu Arg Ile Arg
        260                 265                 270

Asp Phe Ala Ile Gly Ala Arg Ala Leu Gly Glu Arg Phe Ser Leu Thr
    275                 280                 285

Thr Trp
290

(2) INFORMATION FOR SEQ ID NO:2:

(i) SEQUENCE CHARACTERISTICS:
        (A) LENGTH: 290 amino acids
        (B) TYPE: amino acid
        (D) TOPOLOGY: linear (ii) MOLECULE TYPE: protein (vi) ORIGINAL SOURCE:
        (A) ORGANISM: Streptomyces sp.
        (B) STRAIN: TH1

(xi) SEQUENCE DESCRIPTION: SEQ ID NO:2:

Met Arg Ser His Ile Leu Gly Lys Ile Glu Leu Asp Gln Thr Arg Leu
1               5                   10                  15

Ala Pro Asp Leu Ala Tyr Leu Ala Ala Val Pro Thr Val Glu Glu Glu
            20                  25                  30

```
Tyr Asp Glu Phe Ser Asn Gly Phe Trp Lys His Val Pro Leu Trp Asn
             35                  40                  45

Ala Ser Gly Asp Ser Glu Asp Arg Leu Tyr Arg Asp Leu Lys Asp Ala
 50                  55                  60

Ala Ala Gln Pro Thr Ala His Val Glu His Val Pro Tyr Leu Lys Glu
 65                  70                  75                  80

Ile Val Thr Thr Val Phe Asp Gly Thr His Leu Gln Met Ala Arg Ser
             85                  90                  95

Arg Asn Leu Lys Asn Ala Ile Val Ile Pro His Arg Asp Phe Val Glu
            100                 105                 110

Leu Asp Arg Glu Val Asp Arg Tyr Phe Arg Thr Phe Met Val Leu Glu
            115                 120                 125

Asp Ser Pro Leu Ala Phe His Ser Asn Glu Asp Thr Val Ile His Met
130                 135                 140

Arg Pro Gly Glu Ile Trp Phe Leu Asp Ala Ala Thr Val His Ser Ala
145                 150                 155                 160

Val Asn Phe Ser Glu Ile Ser Arg Gln Ser Leu Cys Val Asp Phe Ala
            165                 170                 175

Phe Asp Gly Pro Phe Asp Glu Lys Glu Ile Phe Ala Asp Ala Thr Leu
            180                 185                 190

Tyr Ala Pro Gly Ser Thr Pro Asp Leu Pro Glu Arg Arg Pro Phe Thr
            195                 200                 205

Ala Glu His Arg Arg Arg Ile Leu Ser Leu Gly Gln Val Ile Glu Arg
210                 215                 220

Glu Asn Phe Arg Asp Ile Leu Phe Leu Leu Ser Lys Val His Tyr Lys
225                 230                 235                 240

Tyr Asp Val His Pro Ser Glu Thr Tyr Asp Trp Leu Ile Glu Ile Ser
            245                 250                 255

Lys Gln Ala Gly Asp Glu Lys Met Val Val Lys Ala Glu Gln Ile Arg
            260                 265                 270

Asp Phe Ala Val Glu Ala Arg Ala Leu Ser Glu Arg Phe Ser Leu Thr
            275                 280                 285

Ser Trp
290
```

(2) INFORMATION FOR SEQ ID NO:3:

(i) SEQUENCE CHARACTERISTICS:
        (A) LENGTH: 870 base paires
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Streptomyces sp.
        (B) STRAIN: TH1

(xi) SEQUENCE DESCRIPTION: SEQ ID NO:3:

```
GTGCGCTCGC ACATACTCGG CCGCATTGAA CTCGACCAGG AACGCTTAGG CAGGGACCTC      60

GAATATCTCG CCACGGTGCC CACCGTGGAA GAGGAGTACG ACGAGTTCAG CAACGGGTTC     120

TGGAAGAACA TCCCGCTGTA CAACGCGAGC GGCGGCAGCG AGGACCGGCT GTACCGCGAC     180

CTCGAGGGCT CACCGGCGCA GCCCACCAAA CACGCCGAGC AGGTTCCGTA CCTCAACGAG     240

ATCATCACCA CGGTCTACAA CGGCGAGCGG CTCCAGATGG CGCGTACGCG GAACCTGAAG     300

AACGCCGTCG TCATCCCGCA CCGCGACTTC GTGGAGCTCG ACCGCGAACT CGACCAGTAC     360
```

```
TTCCGCACCC ATTTGATGCT TGAGGACAGC CCGCTGGCCT TCCACTCGGA CGACGACACC    420

GTCATCCACA TGCGGGCCGG CGAGATCTGG TTCCTCGACG CGGCCGCCGT CCACTCGGCC    480

GTCAACTTCG CCGAGTTCAG CAGGCAGTCG CTCTGCGTCG ACCTCGCCTT CGACGGCGCG    540

TTCGACGAGA AGGAAGCCTT CGCGGACGCC ACGGTCTACG CCCCGAACCT CAGCCCCGAC    600

GTCCGCGAAC GCAAGCCGTT CACCAAGGAG CGGGAGGCCG GGATCCTCGC CCTGTCCGGC    660

GTGATCGGAC GCGAGAACTT CCGGGACATC CTCTTTCTGC TGTCCAAGGT CCACTACACC    720

TACGACGTCC ATCCGGGTGA AACCTTCGAG TGGCTCGTGA GCGTCTCCAA GGGTGCGGGA    780

GACGACAAGA TGGTGGAGAA GGCCGAGCGG ATCAGGGACT TCGCCATCGG CGCACGGGCA    840

CTCGGCGAGC GTTTCTCGCT GACCACCTGG                                    870

(2) INFORMATION FOR SEQ ID NO:4:

(i) SEQUENCE CHARACTERISTICS:
        (A) LENGTH: 870 base paires
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Streptomyces sp.
        (B) STRAIN: TH1

(xi) SEQUENCE DESCRIPTION: SEQ ID NO:4:

ATGCGCTCGC ACATCCTTGG CAAGATCGAA CTCGATCAGA CCCGGTTGGC GCCGGATCTC     60

GCATACCTCG CCGCAGTTCC GACCGTGGAG GAGGAGTACG ACGAGTTCAG CAACGGGTTC    120

TGGAAGCACG TGCCCCTGTG GAACGCCTCC GGGGACAGCG AGGACCGGCT CTACCGCGAC    180

CTCAAGGACG CCGCCGCACA GCCGACCGCG CACGTGGAGC ACGTCCCCTA CCTCAAGGAG    240

ATCGTGACCA CGGTCTTCGA CGGCACGCAC CTGCAGATGG CGCGGAGCCG GAACCTGAAG    300

AACGCCATCG TCATCCCGCA CCGCGACTTC GTGGAGCTGG ACCGCGAAGT CGACCGGTAC    360

TTCCGCACGT TCATGGTGCT GGAGGACAGC CCGCTCGCCT TCCACTCGAA CGAGGACACC    420

GTCATCCACA TGCGCCCGGG CGAAATATGG TTCCTGGACG CGGCGACGGT GCACTCCGCG    480

GTCAACTTCT CGGAAATCAG CCGTCAGTCC CTGTGCGTCG ACTTCGCCTT CGACGGTCCC    540

TTCGACGAGA AGGAGATCTT CGCGGACGCC ACCCTCTACG CTCCGGGCTC CACGCCCGAC    600

CTGCCCGAGC GCCGCCCCTT CACCGCGGAG CACCGGCGGC GGATCCTCTC CCTGGGCCAG    660

GTGATCGAGC GGGAGAACTT CCGGGACATT CTGTTCCTGC TGTCCAAGGT GCACTACAAG    720

TACGACGTGC ACCCCAGCGA GACGTACGAC TGGCTGATCG AGATCTCGAA ACAGGCCGGC    780

GACGAGAAGA TGGTCGTGAA GGCGGAGCAG ATCAGGGACT TCGCCGTCGA GGCCCGCGCC    840

CTGAGCGAGC GCTTCTCCCT GACCTCCTGG                                    870

(2) INFORMATION FOR SEQ ID NO:5:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (v) FRAGMENT TYPE: N-terminal fragment (vi) ORIGINAL SOURCE:
        (A) ORGANISM: Streptomyces sp.
        (B) STRAIN: TH1
```

(xi) SEQUENCE DESCRIPTION: SEQ ID NO:5:

Met Arg Ser His Ile Leu Gly Arg Ile Glu Leu Asp Gln Glu Arg Leu
1               5                   10                  15

Gly Arg Asp Leu Glu Tyr Leu Ala Thr Val Pro Thr Val
                20                  25

(2) INFORMATION FOR SEQ ID NO:6:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal fragment (vi) ORIGINAL SOURCE:
        (A) ORGANISM: Streptomyces sp.
        (B) STRAIN: TH1

(xi) SEQUENCE DESCRIPTION: SEQ ID NO:6:

Glu Ala Phe Ala Asp Ala Thr Val Tyr Ala Pro Asn Leu Ser Pro Asp
1               5                   10                  15

Val Arg Glu Arg Lys Pro Phe Thr Lys
                20                  25

(2) INFORMATION FOR SEQ ID NO:7:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (v) FRAGMENT TYPE: internal fragment (vi) ORIGINAL SOURCE:
        (A) ORGANISM: Streptomyces sp.
        (B) STRAIN: TH1

(xi) SEQUENCE DESCRIPTION: SEQ ID NO:7:

Asn Ile Pro Leu Tyr Asn Ala Ser Gly Gly Ser Glu Asp Arg Leu Tyr
1               5                   10                  15

Arg Asp Leu Glu Gly Ser Pro Ala Gln
                20                  25

(2) INFORMATION FOR SEQ ID NO:8:

(i) SEQUENCE CHARACTERISTICS:
        (A) LENGTH: 17 base paires
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:8:

ATGTGYTCNC AYATHYT                                  17

(2) INFORMATION FOR SEQ ID NO:9:

(i) SEQUENCE CHARACTERISTICS:
        (A) LENGTH: 14 base paires
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:9:

GTNGGNACNG TWGC                                                          14

(2) INFORMATION FOR SEQ ID NO:10:

(i) SEQUENCE CHARACTERISTICS:
        (A) LENGTH: 14 base paires
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:10:

GTNGCNAGRT AYTC                                                          14

(2) INFORMATION FOR SEQ ID NO:11:

(i) SEQUENCE CHARACTERISTICS:
        (A) LENGTH: 74 base paires
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:11:

```
ATG TGT TCG CAT ATA CTC GGC CGC ATT GAA CTC GAC CAG GAA CGC TTA          48
Met Cys Ser His Ile Leu Gly Arg Ile Glu Leu Asp Gln Glu Arg Leu
 1               5                  10                  15

GGC AGG GAC CTC GAA TAC CTC GCC AC                                       74
Gly Arg Asp Leu Glu Tyr Leu Ala
                20
```

(2) INFORMATION FOR SEQ ID NO:12:

(i) SEQUENCE CHARACTERISTICS:
        (A) LENGTH: 74 base paires
        (B) TYPE: nucleic acid
        (C) STRANDEDNESS: double
        (D) TOPOLOGY: linear (ii) MOLECULE TYPE: other nucleic acid, synthetic DNA (xi) SEQUENCE DESCRIPTION: SEQ ID NO:12:

```
ATG TGC TCG CAT ATC CTT GGC AAG ATC GAA CTC GAT CAG ACC CGG TTG          48
Met Cys Ser His Ile Leu Gly Lys Ile Glu Leu Asp Gln Thr Arg Leu
 1               5                  10                  15

GCG CCG GAT CTC GAG TAC CTC GCC AC                                       74
Ala Pro Asp Leu Glu Tyr Leu Ala
                20
```

(2) INFORMATION FOR SEQ ID NO:13:

(i) SEQUENCE CHARACTERISTICS:
        (A) LENGTH: 1081 base paires
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Streptomyces sp.
        (B) STRAIN: TH1

(xi) SEQUENCE DESCRIPTION: SEQ ID NO:13:

```
GGTACCCATT CCGTCACCGA AAGCTGAACT CGACACCAGG AGGACGACGC GTGCGCTCGC      60

ACATACTCGG CCGCATTGAA CTCGACCAGG AACGCTTAGG CAGGGACCTC GAATATCTCG     120

CCACGGTGCC CACCGTGGAA GAGGAGTACG ACGAGTTCAG CAACGGGTTC TGGAAGAACA     180

TCCCGCTGTA CAACGCGAGC GGCGGCAGCG AGGACCGGCT GTACCGCGAC CTCGAGGGCT     240

CACCGGCGCA GCCCACCAAA CACGCCGAGC AGGTTCCGTA CCTCAACGAG ATCATCACCA     300

CGGTCTACAA CGGCGAGCGG CTCCAGATGG CGCGTACGCG GAACCTGAAG AACGCCGTCG     360

TCATCCCGCA CCGCGACTTC GTGGAGCTCG ACCGCGAACT CGACCAGTAC TTCCGCACCC     420

ATTTGATGCT TGAGGACAGC CCGCTGGCCT TCCACTCGGA CGACGACACC GTCATCCACA     480

TGCGGGCCGG CGAGATCTGG TTCCTCGACG CGGCCGCCGT CCACTCGGCC GTCAACTTCG     540

CCGAGTTCAG CAGGCAGTCG CTCTGCGTCG ACCTCGCCTT CGACGGCGCG TTCGACGAGA     600

AGGAAGCCTT CGCGGACGCC ACGGTCTACG CCCCGAACCT CAGCCCCGAC GTCCGCGAAC     660

GCAAGCCGTT CACCAAGGAG CGGGAGGCCG GGATCCTCGC CCTGTCCGGC GTGATCGGAC     720

GCGAGAACTT CCGGGACATC CTCTTTCTGC TGTCCAAGGT CCACTACACC TACGACGTCC     780

ATCCGGGTGA AACCTTCGAG TGGCTCGTGA GCGTCTCCAA GGGTGCGGGA GACGACAAGA     840

TGGTGGAGAA GGCCGAGCGG ATCAGGGACT TCGCCATCGG CGCACGGGCA CTCGGCGAGC     900

GTTTCTCGCT GACCACCTGG TAGACGGCCG AAGAACGGGG CCCGGGGGAA CAGTGATCGA     960

GGAGATACTT CCCGTCGACG TGATGTCCGC GGAGGCGTTC GACGACGATG CGGACATCCA    1020

GCTCTTCGCC GAGGAACGCG CGGCCGTCGC CGATGCCGTA CCGCGGCGCC GACGGGAATT    1080

C                                                                   1081

(2) INFORMATION FOR SEQ ID NO:14:

(i) SEQUENCE CHARACTERISTICS:
        (A) LENGTH: 1826 base paires
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Streptomyces sp.
        (B) STRAIN: TH1

(xi) SEQUENCE DESCRIPTION: SEQ ID NO:14:

TCGCGACCTG GAGGGTCGGA TGCGCTCGCA CATCCTTGGC AAGATCGAAC TCGATCAGAC      60

CCGGTTGGCG CCGGATCTCG CATACCTCGC CGCAGTTCCG ACCGTGGAGG AGGAGTACGA     120

CGAGTTCAGC AACGGGTTCT GGAAGCACGT GCCCCTGTGG AACGCCTCCG GGGACAGCGA     180

GGACCGGCTC TACCGCGACC TCAAGGACGC CGCCGCACAG CCGACCGCGC ACGTGGAGCA     240

CGTCCCCTAC CTCAAGGAGA TCGTGACCAC GGTCTTCGAC GGCACGCACC TGCAGATGGC     300

GCGGAGCCGG AACCTGAAGA ACGCCATCGT CATCCCGCAC CGCGACTTCG TGGAGCTGGA     360

CCGCGAAGTC GACCGGTACT TCCGCACGTT CATGGTGCTG GAGGACAGCC CGCTCGCCTT     420

CCACTCGAAC GAGGACACCG TCATCCACAT GCGCCCGGGC GAAATATGGT TCCTGGACGC     480

GGCGACGGTG CACTCCGCGG TCAACTTCTC GGAAATCAGC CGTCAGTCCC TGTGCGTCGA     540

CTTCGCCTTC GACGGTCCCT TCGACGAGAA GGAGATCTTC GCGGACGCCA CCCTCTACGC     600

TCCGGGCTCC ACGCCCGACC TGCCCGAGCG CCGCCCCTTC ACCGCGGAGC ACCGGCGGCG     660

GATCCTCTCC CTGGGCCAGG TGATCGAGCG GGAGAACTTC CGGGACATTC TGTTCCTGCT     720
```

-continued

```
GTCCAAGGTG CACTACAAGT ACGACGTGCA CCCCAGCGAG ACGTACGACT GGCTGATCGA      780

GATCTCGAAA CAGGCCGGCG ACGAGAAGAT GGTCGTGAAG GCGGAGCAGA TCAGGGACTT      840

CGCCGTCGAG GCCCGCGCCC TGAGCGAGCG CTTCTCCCTG ACCTCCTGGT AATGGCGCGA      900

CCTCAGCCCG CGTGACAACA GTTCGGCCCC GGTGGCGCGG NGCGTCCCGG ACGCGCGCCG      960

GNCGCTACCG GACACCGGGG CACGTAGGTG GTGTACCGNC TGNCGGTCTC CGGCAGTCAG     1020

TTGCTGGTTC GACTCCAGCT GCCCCGACCG CCTCGCGCTC GGACGCGACC CCGGGCACCT     1080

CCGNGGGCAC CGCGTTCGCA TCACGGACAC CCCACCCACA CCAGCCGGGC CCACCCGAGG     1140

AGCCAGTTCA CATGTCCAGT GACATACACG CGGCGGCATC CAGACCGATT CCGCCGAAGC     1200

CCGCCGCATC GACGGAGGTC GCGCCGCGCA CGCTGGTCAG CCGGCTGCCC TCGCTGACCG     1260

GCCTGCGCTT CCCGGCGGCG TTCATCGTGT TCCTCTTCCA CGCCTCGCTG CCGTTTCCCG     1320

CGGTGCGCCT GTTCGCCGAC GACGGGGTGG AACACCGCTA CGGGTGGGCC CTCGGCCCGA     1380

GCGGCGCACT CGGCGTGACG TTCTTCTTCG CGCTCAGCGG ATTCGTGCTG ACGTGGTCGG     1440

CTCCCGCCGG CGACACCGCA CCGTCCTTCT GGCGCCGGCG CTTCGTCAAG ATCCTGCCCA     1500

ACTACGTCGT CGCGTGGGTC CTGGCGATGG TGCTGTACGC GGCCGCGACG CCCGTCCTGC     1560

CCGCGCTCGG CGCCCTTTTC ATGCTCCAGG TGTGGACGCC GTACTTCACC GAGCACCTCC     1620

CGGTGAACCC ACCGAGCTGG TCGCTGNCCG TGGAAGCCGT CTTCTATCTG GCCTTCCCGT     1680

TCCTGCTGGC CGGGATCAGA CGGATACCGG CCGCCCGGCT GAAGTACTGG ATCGCCGGCA     1740

CGGTGGCCGC CGTCTTCGCC ACGCCGCTGA TCACCTACCT CCTGGTGCCG GCGGGCCCGC     1800

ACGTGATGCC GGGCACGGGC GGTACC                                         1826
```

(2) INFORMATION FOR SEQ ID NO:15:

(i) SEQUENCE CHARACTERISTICS:
        (A) LENGTH: 312 amino acids
        (B) TYPE: amino acid
        (D) TOPOLOGY: linear (ii) MOLECULE TYPE: protein (vi) ORIGINAL SOURCE:
        (A) ORGANISM: Streptomyces sp.
        (B) STRAIN: TH1

(ix) FEATURE:
        (A) NAME/KEY: peptide
        (B) LOCATION: 23 to 312
        (C) IDENTIFICATION METHOD: by similarity with known sequence
            or to an established consensus (vi) ORIGINAL SOURCE:
        (A) ORGANISM: Escherichia coli (vii) IMMEDIATE SOURCE:pBluescriptIIKS+

(ix) FEATURE:
        (A) NAME/KEY: peptide
        (B) LOCATION: 1 to 21
        (C) IDENTIFICATION METHOD: by similarity with known sequence
            or to an established consensus (xi) SEQUENCE DESCRIPTION: SEQ ID NO:15:

```
Met Thr Met Ile Thr Pro Ser Ala Gln Leu Thr Leu Thr Lys Gly Asn
 1               5                  10                  15

Lys Ser Trp Val Pro Arg Val Arg Ser His Ile Leu Gly Arg Ile Glu
            20                  25                  30

Leu Asp Gln Glu Arg Leu Gly Arg Asp Leu Glu Tyr Leu Ala Thr Val
        35                  40                  45
```

-continued

```
Pro Thr Val Glu Glu Glu Tyr Asp Glu Phe Ser Asn Gly Phe Trp Lys
 50                  55                  60

Asn Ile Pro Leu Tyr Asn Ala Ser Gly Gly Ser Glu Asp Arg Leu Tyr
 65                  70                  75                  80

Arg Asp Leu Glu Gly Ser Pro Ala Gln Pro Thr Lys His Ala Glu Gln
                 85                  90                  95

Val Pro Tyr Leu Asn Glu Ile Ile Thr Thr Val Tyr Asn Gly Glu Arg
                100                 105                 110

Leu Gln Met Ala Arg Thr Arg Asn Leu Lys Asn Ala Val Val Ile Pro
            115                 120                 125

His Arg Asp Phe Val Glu Leu Asp Arg Glu Leu Asp Gln Tyr Phe Arg
130                 135                 140

Thr His Leu Met Leu Glu Asp Ser Pro Leu Ala Phe His Ser Asp Asp
145                 150                 155                 160

Asp Thr Val Ile His Met Arg Ala Gly Glu Ile Trp Phe Leu Asp Ala
                165                 170                 175

Ala Ala Val His Ser Ala Val Asn Phe Ala Glu Phe Ser Arg Gln Ser
                180                 185                 190

Leu Cys Val Asp Leu Ala Phe Asp Gly Ala Phe Asp Glu Lys Glu Ala
            195                 200                 205

Phe Ala Asp Ala Thr Val Tyr Ala Pro Asn Leu Ser Pro Asp Val Arg
210                 215                 220

Glu Arg Lys Pro Phe Thr Lys Glu Arg Glu Ala Gly Ile Leu Ala Leu
225                 230                 235                 240

Ser Gly Val Ile Gly Arg Glu Asn Phe Arg Asp Ile Leu Phe Leu Leu
                245                 250                 255

Ser Lys Val His Tyr Thr Tyr Asp Val His Pro Gly Glu Thr Phe Glu
                260                 265                 270

Trp Leu Val Ser Val Ser Lys Gly Ala Gly Asp Asp Lys Met Val Glu
            275                 280                 285

Lys Ala Glu Arg Ile Arg Asp Phe Ala Ile Gly Ala Arg Ala Leu Gly
290                 295                 300

Glu Arg Phe Ser Leu Thr Thr Trp
305                 310

(2) INFORMATION FOR SEQ ID NO:16:

(i) SEQUENCE CHARACTERISTICS:
        (A) LENGTH: 318 amino acids
        (B) TYPE: amino acid
        (D) TOPOLOGY: linear (ii) MOLECULE TYPE: protein (vi) ORIGINAL SOURCE:
        (A) ORGANISM: Streptomyces sp.
        (B) STRAIN: TH1

(ix) FEATURE:
        (A) NAME/KEY: peptide
        (B) LOCATION: 29 to 318
        (C) IDENTIFICATION METHOD: by similarity with known sequence
            or to an established consensus (vi) ORIGINAL SOURCE:
        (A) ORGANISM: Escherichia coli (vii) IMMEDIATE SOURCE:pBluescriptIIKS+

(ix) FEATURE:
        (A) NAME/KEY: peptide
        (B) LOCATION: 1 to 27
        (C) IDENTIFICATION METHOD: by similarity with known sequence
``` or to an established consensus (xi) SEQUENCE DESCRIPTION: SEQ ID NO:16:

```
Met Thr Met Ile Thr Pro Ser Ala Gln Leu Thr Leu Thr Lys Gly Asn
 1               5                  10                  15

Lys Ser Trp Val Pro Gly Pro Pro Ser Arg Ser Arg Val Arg Ser His
                20                  25                  30

Ile Leu Gly Arg Ile Glu Leu Asp Gln Glu Arg Leu Gly Arg Asp Leu
            35                  40                  45

Glu Tyr Leu Ala Thr Val Pro Thr Val Glu Glu Tyr Asp Glu Phe
     50                  55                  60

Ser Asn Gly Phe Trp Lys Asn Ile Pro Leu Tyr Asn Ala Ser Gly Gly
 65                 70                  75                  80

Ser Glu Asp Arg Leu Tyr Arg Asp Leu Glu Gly Ser Pro Ala Gln Pro
                85                  90                  95

Thr Lys His Ala Glu Gln Val Pro Tyr Leu Asn Glu Ile Ile Thr Thr
                100                 105                 110

Val Tyr Asn Gly Glu Arg Leu Gln Met Ala Arg Thr Arg Asn Leu Lys
            115                 120                 125

Asn Ala Val Val Ile Pro His Arg Asp Phe Val Glu Leu Asp Arg Glu
130                 135                 140

Leu Asp Gln Tyr Phe Arg Thr His Leu Met Leu Glu Asp Ser Pro Leu
145                 150                 155                 160

Ala Phe His Ser Asp Asp Asp Thr Val Ile His Met Arg Ala Gly Glu
                165                 170                 175

Ile Trp Phe Leu Asp Ala Ala Ala Val His Ser Ala Val Asn Phe Ala
                180                 185                 190

Glu Phe Ser Arg Gln Ser Leu Cys Val Asp Leu Ala Phe Asp Gly Ala
                195                 200                 205

Phe Asp Glu Lys Glu Ala Phe Ala Asp Ala Thr Val Tyr Ala Pro Asn
    210                 215                 220

Leu Ser Pro Asp Val Arg Glu Arg Lys Pro Phe Thr Lys Glu Arg Glu
225                 230                 235                 240

Ala Gly Ile Leu Ala Leu Ser Gly Val Ile Gly Arg Glu Asn Phe Arg
                245                 250                 255

Asp Ile Leu Phe Leu Leu Ser Lys Val His Tyr Thr Tyr Asp Val His
                260                 265                 270

Pro Gly Glu Thr Phe Glu Trp Leu Val Ser Val Ser Lys Gly Ala Gly
            275                 280                 285

Asp Asp Lys Met Val Lys Ala Glu Arg Ile Arg Asp Phe Ala Ile
290                 295                 300

Gly Ala Arg Ala Leu Gly Glu Arg Phe Ser Leu Thr Thr Trp
305                 310                 315
```

(2) INFORMATION FOR SEQ ID NO:17:

(i) SEQUENCE CHARACTERISTICS:
       (A) LENGTH: 328 amino acids
       (B) TYPE: amino acid
       (D) TOPOLOGY: linear (ii) MOLECULE TYPE: protein (vi) ORIGINAL SOURCE:
       (A) ORGANISM: Streptomyces sp.
       (B) STRAIN: TH1

(ix) FEATURE:
       (A) NAME/KEY: peptide (B) LOCATION: 38 to 328
(C) IDENTIFICATION METHOD: by similarity with known sequence or to an established consensus (vi) ORIGINAL SOURCE:
(A) ORGANISM: Escherichia coli (vii) IMMEDIATE SOURCE:pBluescriptIIKS+

(ix) FEATURE:
(A) NAME/KEY: peptide
(B) LOCATION: 1 to 37
(C) IDENTIFICATION METHOD: by similarity with known sequence or to an established consensus (xi) SEQUENCE DESCRIPTION: SEQ ID NO:17:

```
Met Thr Met Ile Thr Pro Ser Ala Gln Leu Thr Leu Thr Lys Gly Asn
 1               5                  10                  15

Lys Ser Trp Val Pro Gly Pro Pro Ser Arg Ser Thr Val Ser Ile Ser
                20                  25                  30

Leu Ile Ser Asn Ser Arg Val Arg Ser His Ile Leu Gly Arg Ile Glu
             35                  40                  45

Leu Asp Gln Glu Arg Leu Gly Arg Asp Leu Glu Tyr Leu Ala Thr Val
         50                  55                  60

Pro Thr Val Glu Glu Glu Tyr Asp Glu Phe Ser Asn Gly Phe Trp Lys
 65                  70                  75                  80

Asn Ile Pro Leu Tyr Asn Ala Ser Gly Gly Ser Glu Asp Arg Leu Tyr
                 85                  90                  95

Arg Asp Leu Glu Gly Ser Pro Ala Gln Pro Thr Lys His Ala Glu Gln
                100                 105                 110

Val Pro Tyr Leu Asn Glu Ile Ile Thr Thr Val Tyr Asn Gly Glu Arg
            115                 120                 125

Leu Gln Met Ala Arg Thr Arg Asn Leu Lys Asn Ala Val Val Ile Pro
        130                 135                 140

His Arg Asp Phe Val Glu Leu Asp Arg Glu Leu Asp Gln Tyr Phe Arg
145                 150                 155                 160

Thr His Leu Met Leu Glu Asp Ser Pro Leu Ala Phe His Ser Asp Asp
                165                 170                 175

Asp Thr Val Ile His Met Arg Ala Gly Glu Ile Trp Phe Leu Asp Ala
                180                 185                 190

Ala Ala Val His Ser Ala Val Asn Phe Ala Glu Phe Ser Arg Gln Ser
            195                 200                 205

Leu Cys Val Asp Leu Ala Phe Asp Gly Ala Phe Asp Glu Lys Glu Ala
        210                 215                 220

Phe Ala Asp Ala Thr Val Tyr Ala Pro Asn Leu Ser Pro Asp Val Arg
225                 230                 235                 240

Glu Arg Lys Pro Phe Thr Lys Glu Arg Glu Ala Gly Ile Leu Ala Leu
                245                 250                 255

Ser Gly Val Ile Gly Arg Glu Asn Phe Arg Asp Ile Leu Phe Leu Leu
            260                 265                 270

Ser Lys Val His Tyr Thr Tyr Asp Val His Pro Gly Glu Thr Phe Glu
        275                 280                 285

Trp Leu Val Ser Val Ser Lys Gly Ala Gly Asp Asp Lys Met Val Glu
290                 295                 300

Lys Ala Glu Arg Ile Arg Asp Phe Ala Ile Gly Ala Arg Ala Leu Gly
305                 310                 315                 320

Glu Arg Phe Ser Leu Thr Thr Trp
                325
```